(12) United States Patent
Lange

(10) Patent No.: US 6,898,582 B2
(45) Date of Patent: May 24, 2005

(54) METHOD AND APPARATUS FOR EXTRACTING LOW SNR TRANSIENT SIGNALS FROM NOISE

(75) Inventor: Daniel H. Lange, Kfar Vradim (IL)

(73) Assignee: Algodyne, Ltd., Herzliya Pituach (IL)

( * ) Notice: Subject to any disclaimer, the term of this patent is extended or adjusted under 35 U.S.C. 154(b) by 357 days.

(21) Appl. No.: 09/965,446

(22) Filed: Sep. 26, 2001

(65) Prior Publication Data

US 2004/0015894 A1 Jan. 22, 2004

Related U.S. Application Data

(63) Continuation of application No. 09/223,389, filed on Dec. 30, 1998.

(51) Int. Cl.[7] .............................................. G06F 15/18
(52) U.S. Cl. .............................. 706/14; 706/15; 706/30
(58) Field of Search .............................. 706/14, 15, 30

(56) References Cited

U.S. PATENT DOCUMENTS

| | | | |
|---|---|---|---|
| 4,667,513 | A | 5/1987 | Konno |
| 4,697,599 | A | 10/1987 | Woodley et al. |
| 4,844,091 | A | 7/1989 | Bellak |
| 5,018,526 | A | 5/1991 | Gaston-Johansson |
| 5,069,218 | A | 12/1991 | Ikeda |
| 5,092,343 | A | 3/1992 | Spitzer et al. |
| 5,150,323 | A | 9/1992 | Castelaz |
| 5,402,520 | A | 3/1995 | Schnitta |

(Continued)

FOREIGN PATENT DOCUMENTS

| | | |
|---|---|---|
| DE | 30 04 126 A1 | 8/1981 |
| JP | 7023964 | 1/1995 |
| WO | WO 98/16152 | 4/1998 |

OTHER PUBLICATIONS

M. Abeles, Y. Prut, E. Vaadia, and A. Aertsen, "Integration, synchronicity and periodicity," in *Brain Theory: Spatio—Temporal Aspects of Brain Function*, A. Aertsen Ed., Elsevier Science Publishers B.V., 1993, pp. 149–181.

H. Akaike, "Statistical predictor identification," *Ann. Inst. Stat. Math.*, vol. 22, pp. 203–217. 1970.

J.I. Aunon, C.D. McGillem, and D.G. Childers, "Signal processing in evoked potential research: averaging and modeling," CRC *Crit. Rev. Bioeng.*, vol. 5, pp. 323–367, 1981.

E.A. Bartnik, K.J. Blinowska, and P.J. Durka, "Single evoked potential reconstruction by means of wavelet transform," *Biol. Cybern.*, vol. 67, pp. 175–181, 1992.

H.A. Beagly, B.M. Sayers, and A.J. Ross, Fully objective ERA by phase spectral analysis, *Acta Otolaryngol*, vol. 87, pp. 270–278, 1979.

(Continued)

*Primary Examiner*—Anthony Knight
*Assistant Examiner*—Joseph P. Hirl
(74) *Attorney, Agent, or Firm*—Jones Day

(57) ABSTRACT

A method and apparatus for processing a composite signal generated by a transient signal generation mechanism to extract a repetitive low SNR transient signal, such as an evoked potential (EP) appearing in an electroencephalogram (EEG) generated in response to sensory stimulation, by: (a) dynamically identifying, via a learning process, the major transient signal types in the composite signal; (b) decomposing the identified major transient signal types into their respective constituent components; (c) synthesizing a parametric model emulating the transient signal generation mechanism; and (d) utilizing the model and the constituent components to identify and extract the low SNR transient signal from the composite signal.

25 Claims, 25 Drawing Sheets

U.S. PATENT DOCUMENTS

| | | | |
|---|---|---|---|
| 5,533,514 A | 7/1996 | Lavigne et al. | |
| 5,617,513 A | 4/1997 | Schnitta | |
| 5,634,472 A | 6/1997 | Raghuprasad | |
| 5,687,291 A | 11/1997 | Smyth | |
| 5,692,500 A | 12/1997 | Gaston-Johansson | |
| 5,742,694 A | 4/1998 | Eatwell | |
| 5,846,208 A | 12/1998 | Pichlmayr et al. | |
| 5,873,900 A | 2/1999 | Maurer et al. | |
| 5,878,389 A | 3/1999 | Hermansky et al. | |
| 5,916,172 A | 6/1999 | Hodges et al. | |
| 5,941,833 A | 8/1999 | Lipman | |
| 5,995,868 A | * 11/1999 | Dorfmeister et al. | ....... 600/544 |
| 6,018,675 A | 1/2000 | Apkarian et al. | |
| 6,044,303 A | 3/2000 | Agarwala et al. | |
| 6,047,202 A | 4/2000 | Finneran et al. | |
| 6,067,567 A | 5/2000 | Bartfai et al. | |
| 6,105,015 A | 8/2000 | Nguyen et al. | |
| 6,113,552 A | 9/2000 | Shimazu et al. | |
| 6,128,346 A | 10/2000 | Suarez et al. | |
| 6,146,334 A | 11/2000 | Laserow | |
| 6,168,569 B1 | 1/2001 | McEwen et al. | |

OTHER PUBLICATIONS

G.E. Birch, P.D. Lawrence, and R.D. Hare, "Single–trial processing of event related potentials using outlier information," *IEEE Trans. Biomed. Eng.*, vol. 40, pp. 59–73, 1993.

G.E.P. Box and G.M. Jenkins, *Time series analysis: forecasting and control*. San Francisco, CA: Holden–Day, 1976, E.H. Carlton and S. Katz, "Is wierner filtering an effective method of improving evoked potential estimation ? ," *IEEE Trans. Biomed. Eng.*, vol. 34, No. 1, 1987.

S. Cerutti, G. Baselli, D. Liberati, G. Pavesi, "Single sweep analysis of visual evoked potentials through a model of parametric identification," *Biol. Cybernetics* , vol. 56, pp. 111–120, 1987.

S. Cerutti, G. Chiarenza, D. Liberati, P. Mascellani, and G. Pavesi, "A parametric method of identification of single trial event related potentials in the brain," *IEEE Trans. Biomed. Eng.*, vol. 35, pp. 701–711, 1988.

K.H. Chiappa, *Evoked potentials in clinical medicine*. New York: Raven, 1983.

V.H. Clarson and J.J. Liang, "Mathematical classification of evoked potential waveforms," *IEEE Trans. Sys. Man & Cybern.*, vol. 19, pp. 68–73, 1989.

A.M. Dale and M.I. Sereno, "Improving localization of cortical activity by combining EEG and MEG with MRI cortical surface reconstruction: a linear approach," *Journal of Cognitive Neuroscience*, vol. 5, 162–176, 1993.

J.P.C. de Weerd, "A posteriori time–varying filtering of averaged evoked potentials. I. Introduction and conceptual basis," *Biol. Cybernetics.*, vol. 41, pp. 211–222, 1981.

L. Deecke, B. Grozinger, and H.H. Kornhuber, "Voluntary finger movement in man: cerebral potentials and theory," *Biol. Cybernetics*, vol. 23, pp. 99–119, 1976.

E. Donchin, "A Multivariate approach to the analysis of average evoked potentials," *IEEE. Trans. Biomed. Eng.*, vol. 13, pp. 131–139, 1966.

E. Donchin and E. Heffley, "Multivariate analysis of event-related potential data: a tutorial review" in *Multidisciplinary perspectives in event–related brain potential research*, D. Otto (Ed.), Washington D.C. : Government Printing Office, pp. 555–572, Dec. 1978.

D.J. Doyle, "Some comments on the use of wiener filtering in the estimation of evoked potentials," *Electroencephalogr. Clin. Neurophysiol.*, vol. 28, pp. 533–534, 1975.

R.O. Duda and P.E. Hart. Pattern *classification and scene analysis*. Wiley: New–York, 1976.

L.A. Farwell and E. Donchin, "Taking off the top of your head: toward a mental prosthesis utilyzing event–related potentials," *Electroencephalogr. Clin. Neurophysiol.*, vol. 70, pp. 510–523, 1988.

L.A. Farwell and E. Donchin, "The truth will out: Interrogative polygraphy with event related brain potentials," *Psychophysiology*, vol. 28, 1991.

J.A. Freeman and D.M. Skapura. *Neural networks: Algorithms, applications, and programming techniques*: Addison–Wesley Publishing Company, USA, pp. 531–547, 1992.

M. Furst and A. Blau, "Optimal a–posteriori time domain filter for average evoked potentials," *IEEE Trans. Biomed. Eng.*, vol. 38, pp. 827–833, 1991.

W. Gersch, "Spectral analysis of EEG's by autoregressive decomposition of time series," *Math. Biosc.* vol. 7, pp. 205–222, 1970.

A.S. Gevins, "Analysis of the electromagentic signals of the human brain: milestones, obstacles and goals," *IEEE Trans. Biomed. Eng.* , vol. 31, pp. 833–850, 1984.

A.S. Gevins, N.H. Morgan, S.L. Bressler, J.C. Doyle, and B. A. Cutillo, "Improved event related potential estimation using statistical pattern classification," *Electroencephalogr. Clin. Neurophysiol.*, vol. 64, pp. 177–186, 1986.

G.H. Golub and C.F. Van Loan, *Matrix computations*. Johns Hopkins University Press, Balti–more, MD, 1983.

L. Gupta, D. L. Molfese, R. Tammana, and P. G. Simos, "Nonlinear alignment and averaging for estimating the evoked potential," *IEEE Trans. Biomed. Eng.*, vol. 43, pp. 348–356, 1996.

S. Haykin, *Adaptive filter theory*. Prentice–Hall: N.J., 1986.

S. Haykin. *Neural Networks: A Comprehensive Foundation*: Macmillan College Publishing Company, Inc., USA, 1994.

J. Hertz, A.. Krogh, and R.G. Palmer. *Introduction to the theory of neural computation*. Addison–Wesley Publishing Company, USA, 1991.

H.H. Jasper, "The ten–twenty electrode system of the international federation," *Electroenc. Clin. Neurophysiol.*, vol. 10, pp. 371–375, 1958.

J.P. Kaipio and P.A. Karjalainen, "Estimation of event related synchronization changes by a new tvar method," *IEEE Trans. Biomed. Eng.*, vol. 44, pp. 649–656, 1997.

X. Kong and N.V. Thakor, "Adaptive Estimation of Latency Changes in Evoked Potentials," *IEEE Trans. Biomed. Eng.*, vol. 43, pp. 189–197, 1996.

R. Kristeva, D. Cheyne, W. Lang, G. Lindinger, and L. Deecke, "Movement related potentials accompanying unilateral and bilateral finger movements with different inertial loads," *Electroencephalogr. Clin. Neurophysiol.*, vol. 75, pp. 410–418, 1979.

R. Kristeva, E. Keller, L. Deecke and H.H. Kornhuber, "Cerebral potentials preceding unilateral and bilateral simultaneous finger movement, " *Electroencephalogr. Clin. Neurophysiol.*, vol. 47, pp. 229–238, 1979.

P. Laguna, R. Jane', O. Meste, P.W. Poon, P. Caminal, H. Rix, and N.V. Thakor, "Adaptive filter for event–related bioelectric signals using an impulse correlated reference input: comparison with signal averaging techniques," *IEEE Trans. Biomed. Eng.* , vol. 39, pp. 1032–1043, 1992.

D.H. Lange, H. Pratt, and G.F. Inbar, "Segmented matched filtering of singe event related evoked potentials," *IEEE Trans. Biomed. Eng.*, vol. 42, pp. 317–321, 1995.

D.H. Lange and G.F. Inbar, "A robust parametric estimator for single–trial movement related brain potentials," *IEEE Trans. Biomed. Eng.*, vol. 43, pp. 341–347, 1996.

D.H. Lange and G.F. Inbar. "Parametric modeling and estimation of amplitude and time shifts in single evoked potential components". In *Advances in Processing and Pattern Analysis of Biological Signals*, L Gath and G. F. Inbar, Eds. Plenum Press: 1996.

D.H. Lange and G.F. Inbar, "Brain–wave based polygraphy," in *Proc. IEEE EMBS96*, Amsterdam, 1996.

D.H. Lange, H. Pratt, and G.F. Inbar, "Modeling and estimation of single evoked brain potential components," *IEEE Trans. Blomed. Eng.*, vol. 44, pp. 791–799, 1997.

D.H. Lange, H.T. Siegelman, H. Pratt, and G.F. Inbar, "A generic approach for identification of event related brain potentials via a competitive neural network structure," to appear in Proc. NIPS*7—*Neural Information and Processing Systems: Natural & Synthetic*, 1998.

D. Liberati, S. DiCorrado, and S. Mandelli, "Topographic mapping of single sweep evoked potentials in the brain," *IEEE Trans. Biomed. Eng.* , vol. 39, pp. 943–951, 1992.

P.G. Madhaven, "Minimal repetition evoked potential by modified adaptive line enhancement," *IEEE Trans. Biomed. Eng.*, vol. 39, pp. 760–764, 1992.

J. Makhoul, "Linear prediction: a tutorial review," *Proc. IEEE*, vol. 63, pp. 561–580, 1975.

S.G. Mason, G.E. Birch, and M.R. Ito, "Improved single–trial signal extraction of low SNR events," *IEEE Trans. Sig. Proc.*, vol. 42, pp. 423–426, 1994.

G. McCarthy and E. Donchin, "A Metric for Thought: A Comparison of $P_{300}$ Latency and Reaction Time," *Science*, vol. 211, pp. 77–80 , 1981.

H.J. Michalewski, D.K. Prasher, and A. Starr, "Latency variability and temporal interrelationships of the auditory event–related potentials (N1,P2,N2, and P3) in normal subjects," *Electroenc. Clin. Neuropysiol.*, vol. 65, pp. 59–71, 1986.

O. Meste and H. Rix, "Jitter statistics estimation in alignment processes," *Signal Processing*, vol. 51, pp. 41–53, 1996.

J.M. Moser and J.I. Aunon, "Classification and detection of single evoked brain potentials using time–frequency amplitude features," *IEEE Trans. Biomed. Eng*, vol. 33, pp. 1096–1106, 1986.

M. Nakamura, "Waveform estimation from noisy signals with variable signal delay using bispectrum averaging," *IEEE Trans. Biomed. Eng.*, vol. 40, pp. 118–127, 1993.

P.L. Nunez, *Electric fields of the brain*. Oxford University Press, 1981.

T.W. Picton and S.A. Hillyard, "Endogenous event related potentials," in *Handbook of electroencephalographic clinical neurophysiology*, vol. 3, T. W. Picton, Ed. Amsterdam: Elsevier, 1988, pp. 361–426.

D. Popivanov and I. Krekule, "Estimation of homogenity of a set of evoked potentials with respect to its dispersion," *Electroencephalogr. Cln. Neurophysiol*, vol. 55. pp. 606–608, 1983.

H. Pratt, H.J. Michalewski, G. Barrett, and A. Starr, "Brain potentials in memory–scanning task: modality and task effects on potentials to the probes," *Electroencephalogr. Cln. Neuro physiol.*, vol. 72, pp. 407–421, 1989.

M.A. Rodriguez, R.H. Willliams, and T.J. Carlow, "Signal delay and waveform estimation using unwarpped phase averaging," *IEEE Trans. Acoust. Sp. & Sig. Proc.*, vol. 29, pp. 508–513, 1981.

O. Rompelman and H.H. Ros, "Coherent averaging technique: a tutorial review. Part 1: Noise reduction and the equivalent filter," *J. Biomed. Eng.*, vol. 8, pp. 24–29, 1986.

O. Rompelman and H.H. Ros, "Coherent averaging technique: a tutorial review. Part 2 Trigger jitter, overlapping responses and non–periodic stimulation" *J. Biomed. Eng.*, vol. 8 pp. 30–35, 1986.

A.V. Rotterdam., "Limitations and difficulties in signal processing by means of the principal component analysis," *IEEE Trans. Biomed. Eng.* , vol. 17, pp. 268–269, 1970.

D.E. Rumelhart and D. Zipser, "Feature discovery by competitive learning," *Cognitive Science* vol. 9, pp. 75–112, 1985.

V.L. Schwent and S.A. Hillyard, "Evoked potential correlates of selective attention with multi channel auditory inputs," *Electroencephalogr. Clin. Neurophysiol.*, vol. 38, pp. 131–138, 1975.

M.V. Spreckelsen and B. Bromm, "Estimation of single–evoked cerebral potentials by means o parametric modeling and kalman filtering," *IEEE Trans. Biomed. Eng.*, vol. 35, pp. 691–700 1988.

O. Svensson, "Tracking of changes in latency and amplitude of the evoked potential by using adaptive LMS filters and exponential averagers," *IEEE Trans. Biomed. Eng.*, vol. 40, pp 1074–1079, 1993.

N.V. Thakor, "Adaptive filtering of evoked potentials," *IEEE Trans. Biomed. Eng.* , vol. 34, pp. 6–12, 1987.

N.V. Thakor, X.R. Guo, C.A. Vaz, P. Laguana, R. Jane, P. Caminal, H. Rix, and D.F. Hanley "Orthonormal (Fourier and Walsh) models of time varying evoked potentials in neurologic injury," *IEEE Trans. Biomed. Eng.* , vol. 40, pp. 213–221, 1993.

H.G. Vaughan, Jr. and J.C. Arezzo, "The neural basis of event related potentials," in Handbook of *Electroenceph. and Clin. Neurophysiol.*, vol. 3, T.W. Picton Ed., Amsterdam: Elsevier 1998 pp. 45–87.

R.S. Varga, *A Decomposition technique for signals overlapping in time*. Ph.D. dissertation University of Florida, 1969.

C.A. Vaz and N.V. Thakor, Adaptive fourier estimation of time–Varying evoked potentials, *IEEE Trans. Biomed–Eng.*, vol. 3, pp. 448–455, 1989.

R. Verleger and E. Wascher, "Fitting ex–Gauss functions to P3 waveshapes: an attempt distinguishing between real and apparent changes of P3 latency," *Journal of Psychophysiology* vol. 9, pp. 146–158, 1995.

D.O. Walter, "A posteriori wiener filtering of average evoked responses," *Electroencephalog Clin. Neurophysiol.*, suppl., vol. 27, pp. 61–70, 1969.

C.D. Woody, "Characterization of an adaptive filter for the analysis of variable latency neuroelectric signals," *Med. & Biol. Eng.*, vol. 5, pp. 539–5531 1967.

K. Yu and C.D. McGillem, "Optimum filters for estimating evoked potential waveforms," *IEEE Trans. Biomed. Eng.*, vol. 30, pp. 730–737, 1983.

Feng, X.; Schulteis, J., *Identification of high noise lime series signals using hybrid ARMA modeling and neural network approach*, Neural Networks, 1993., IEEE International Conference on Mar. 28–Apr. 1, 1993, p.(s): 1780–1785, vol. 3.

Mitra, S.; Pemmaraju, S., *Efficient coding by neuro–fuzzy clustering in vector quantization of wavelet decomposed signals*, Fuzzy Information Processing Society, 1996. NAFIPS., 1996 Biennial Conference of the North American, Jun. 19–22, 1996, p.(s): 229–233.

Ming–Yao Yang; Wei–Chih Hu; Liang–Yu Shyu, *ECG Events Defection and Classification Using Wavelet and Neural Networks*, Engineering in Medicine and Biology Society, 1997. Proceedings of the 19th Annual International Conference of the IEEE vol. : 1, Oct. 30–Nov. 2, 1997, p.(s): 280–281.

Hara, K.; Nakayama, K., *Classification Of Multi–frequency Signals With Random Noise Using Multileyr Neural Networks*, Neural Networks, Oct. 25–29, 1993. IJCNN '93–Nagoya. Proceedings of 1993 International Joint Conference on, vol.: 1, p.(s): 601–604.

Schnaufer, B.A.; Jenkins, W.K., *Adaptive fault tolerance for reliable LMS adaptive filtering*, Circuits and Systems II: Analog and Digital Signal Processing, IEEE Transactions on, vol.: 44 Dec. 12, 1997, p.(s): 1001–1014.

W.W.L. Keerthipala; Low Tah Chong; Tham Chong Leong, *Artificial neural network model for analysis of power system harmonics*, Neural Networks, 1995. Proceedings., IEEE International Conference on, vol.: 2, Nov. 27–Dec. I, 1995, p.(s): 905–910 vol. 2.

Hara, T.—Itoh, A.; Yatsuka, K.; Kishi, K.; Hirotsu, K., *Application of the neural network to detecting corona discharge occurring in power cables*, Neural Networks to Power Systems, 1993. ANNPS'93., Proceedings of the Second International Forum on Applications of, Apr. 19–22, 1993, p.(s): 259–264.

Buhmann, J.M., Hofmann, T., *Robust vector quantization by competitive learning*, Acoustics, Speech, and Signal Processing 1997. ICASSP–97., 1997 IEEE International Conference on, vol.: 1, Apr. 21–24, 1997, p.(2): 139–142 vol. 1.

Manjunath, B.S.; Chellappa, R., *A unified approach to boundary perception: edges, textures, and illusory contours*, Neural Networks, IEEE Transactions on, vol.: 4 Jan. 1, 1993, p.(s): 96–108.

* cited by examiner-

Layer 2:

Synthesized EP

Decomposed EP

Synthesized EP

Decomposed EP

METHOD AND APPARATUS FOR EXTRACTING LOW SNR TRANSIENT SIGNALS FROM NOISE

CROSS REFERENCE TO RELATED APPLICATIONS

This application is a continuation application of U.S. application Ser. No. 09/223,389, filed on Dec. 30, 1998.

FIELD AND BACKGROUND OF THE INVENTION

The present invention relates to a method and apparatus for extracting low SNR (signal to noise ratio) transient signals from noise. The invention is particularly useful in identifying and extracting low, evoked potential (EP) signals appearing in an electroencephalogram (EEG) of a living being generated in response to sensory stimulation of the nervous system of the living being. The invention is therefore described below with respect to this applications, but it will be appreciated that the invention could also be used in other applications.

1 Introduction

1.1 Preface
1.1.1 The Central Nervous System

The Central Nervous System (CNS) consists of the spinal cord lying within the bony vertebral column, and its continuation, the brain, lying within the skull. The brain is the greatly modified and enlarged part of the CNS, surrounded by three protective membranes and enclosed within the cranial cavity of the skull. Both the brain and spinal cord are bathed in a special extracellular fluid called cerebral spinal fluid.

Within the CNS there are ascending sensory nerve tracts that run from the spinal cord to various areas of the brain, transferring information regarding changes in the external environment of the body that are reported by various sensory transducers; reciprocally, descending motor nerve tracts that originate in various brain structures such as the cerebrum and cerebellum, transfer motor commands to the motor neurons in the spinal cord. These motor neurons control the activation of the skeletal muscles.

Thus there exists a two-way communication link between the brain and spinal cord, allowing higher brain centers to modify or control the spinal behavior as well as to be informed of peripheral events. Information is transmitted to the brain by means of a frequency modulated train of nerve impulses, where the decision to implement a motor action in response to the initial stimulus is manifested in the activity of cortical neurons from various areas of the brain. Such cortical activity is reflected in changes of the field potentials recorded from the brain [Nunez, 1981].

1.1.2 The Brain

The human brain can generally be divided into three main divisions: the brainstem, the cerebellum, and the cerebrum. The brainstem, being the evolutionarily oldest part of the brain, is the medium through which neuronal pathways travel in both directions between the spinal cord and higher brain centers. The thalamus is located at the top and to the side of the brainstem, serving as a relay site responsible for integrating sensory input to the cortex. The cerebellum, which resides on top and to the back of the brainstem, is involved in the fine control of muscle movements. The outer portion of the cerebrum, the cerebral cortex, is a structure about 2 mm thick, having a total area of roughly 2000 cm$^2$ and containing about $10^{10}$ nerve cells. When we consider that brain function involves a continuously changing state of these $10^{10}$ interacting cells we encounter large numbers that transcend our everyday experience and have been compared to the number of stars in the universe.

Much of our conscious experience must involve, in some largely unknown manner, the interaction of cortical neurons. The cortex is also believed to be the structure that generates all but the lowest magnitude electrical potentials which are measured on the scalp. The recorded electrical activity of the human brain, a manifestation of the neurological processes underlying the active interaction between man and nature, has long been used in brain and nervous system research. One major branch is the field of Evoked Potential (EP) research, utilizing specific brain responses as a window into brain function. The contribution of this work lies within the scope of this branch.

1.2 The Electrical Activity of the Brain

The electrical activity of the brain may be divided into three main categories: spontaneous potentials such as alpha or sleep rhythms, evoked potentials representing the response to some stimulus, and potentials generated by single neurons and recorded with micro-electrodes. Although an evoked potential recording represents only a gross measurement of the electrical brain activity, and its neural origins cannot be localized with the precision of single-cell recordings, it does provide a non-invasive and risk-free means of objective brain function investigation in behaving humans. Moreover, it enables tracking of compound brain processes which may not be observable in single-cell recordings due to the vast number of cells involved. This work deals with non-invasive techniques only and does not discuss single-cell recordings.

1.2.1 The ElectroEncephaloGram

Recording the electrical potential differences between an exploring electrode resting on the cortical surface or on the outer surface of the head and a distant reference electrode, in effect registers the resultant field potential at a boundary of a large conductive medium, containing a gigantic multitude of active elements. Under normal circumstances, conducted action potentials in axons contribute little to surface cortical records, as they usually appear asynchronously in time in large numbers of axons, running in many directions relative to the surface. Thus their net influence on potential at the surface is negligible.

An exception occurs when a response is evoked by the simultaneous stimulation of a cortical input, as in the case of direct stimulation of thalamic nuclei or their afferent pathways which project directly to the cortex via thalamocortical axons [Varghan & Arezzo, 1988]. Electrophysiologists have shown that surface records obtained under other circumstances reflect principally the net effect of local post-synaptic potentials of cortical cells. These may be of either sign (excitatory or inhibitory), and may occur directly underneath the electrode or at some distance from it. A potential change recorded at the surface is a measure of the net potential drop between the surface site and the distant reference electrode. Obviously, if all the cell bodies and dendrites of cortical cells were randomly arranged in the cortical structure, the net influence of the synaptic currents would be zero. Any electrical change recorded at the surface must thus be due to the orderly and symmetric arrangement of some class of cells within the cortex.

It should be noted that in the absence of specific external stimulation or definitive mental or motor task, the EEG is considered intrinsic or spontaneous, even though it is recognized to reflect a sum of responses to a myriad of external stimuli and endogenous processes such as somatic movement or mental processes. This is important in the definition of evoked potentials and should be considered in the context of evoked potential extraction principles.

1.2.2 Evoked Potentials

The Neurophysiology of EP's

Evoked Potentials may be divided into several types, according to stimulus or event modality: visual, auditory, somatosensory, motor and cognitive potentials. The brain responses may be short, middle, or long latency, ranging from a few msec to hundreds of msec [Vanghan & Arezzo, 1988].

Cortical responses are generated by primary sensory areas as well as higher cortical areas They have latencies of over 10 msec and amplitudes in the order of 10 microvolts or more. Cortical EP's are usually recorded with near-field recording methods, where the electrodes are placed close to the suspected generators. Subcortical EP's are generated by chains of neurons along sensory pathways leading to cortical receiving areas. These EP's are characterized by short latencies of less than 20 msec. As the brainstem and spinal cord are relatively far away from the recording surface, their activities are much attenuated by intervening tissue. They reach amplitudes of less than 1 microvolt at the surface recording electrodes, and must be recorded with far-field methods which are not sensitive to electrode location as long as the recording electrodes are distant from each other.

EP Definition

Evoked Potentials (EP's) are defined as averaged electric responses of the nervous system to sensory stimulation [Gevins, 1984]. They consist of a sequence of transient waveforms, each with its own morphology, latency, and amplitude. In clinical settings, EP's are elicited by visual or auditory stimulation, or by electric stimulation of sensory nerves [Chiappa, 1983]. These EP's are usually recorded from the scalp, although in special cases like during brain surgery, electrodes may be placed on the surface of the brain or even deep in nerve tissue. The term Event Related Potential (ERP) is now commonly used to denote both EP as well as other brain responses that are the result of cognitive processes accompanying and following stimuli, or of preparatory mechanisms preceding motor action. However, due to historical reasons and to avoid confusion, I will generally use the term EP for all types of brain responses including ERP.

EP Components

When dealing with transient EP's, one must realize that the evoked responses constitute complex waveforms which may include several, possibly overlapping, signal components. Two basic approaches are used for defining EP components: the first is based on peak analysis, where a peak is defined by the most positive or most negative voltage within a specified time interval; the second approach, adopted in this work, attempts to relate the concept of a component to neuronal population of specific localization and electric orientation which becomes active during the performance of specific processing. The decomposition problem of the global response into its constituent components cannot be solved without introducing constraints to reduce the dimensionality of this ill-posed inverse problem. This issue becomes essential if variability analysis of EP's is required [Donchin, 1966].

EP Analysis

The shape, size, and timing of an EP recorded from the scalp or skin depend on many factors, including the duration of the potential scalp responses to single stimuli, which are usually of a very low amplitude, and thus may be partly or totally obscured by the ongoing background EEG activity. The conventional method of EP extraction is synchronous averaging of repeatedly elicited responses, where the uncorrelated EEG contribution averages out and thus enhancing the neural activity that is time-locked to the stimulus. This is true, provided that the time-locked responses remain identical throughout the session [Aunon et. al., 1981; Rompelman & Ross, 1986a]. In practice, however, responses are never identical and trial to trial variability may in fact be quite substantial. Signal variability may be encountered due to a variety of reasons, such as variability due to different behavioral outcome with identical stimuli, or progressive changes in the evoked potential morphology due to factors like sensory adaptation or variable performance. Therefore, the basic assumption underlying signal averaging is usually violated, though its effect may be somewhat reduced with moving-average techniques. This prevents tracking and analysis of dynamic brain processes, which calls for improved methods that would enable analysis of evoked potential waveforms on a single-trial basis.

Several estimation procedures have been recently proposed in attempt to improve the signal to noise ratio of single evoked potential measurements [e.g. Bartnik et. al., 1992; Birch et. al., 1993; Cerutti et. al., 1987; Lange & Inbar, 1996a; Spreckelsen & Bromm, 1988]; however, most of these methods assume constant wave-shapes of the single evoked responses and do not deal with variations of specific components within the EP complex. Some methods are claimed to have the ability to track changes of the evoked responses, but the tracking is limited to global amplitude and latency variations of the entire complex, or at best to only small morphological variations of the EP complex.

1.3 The Single-Trial Estimation Problem

Evoked brain potentials are typically generated in response to afferences originating from peripheral receptors as a result of external stimulation, like somatosensory, visual, and auditory brain potentials, or present a slow evolving activity observed before voluntary movements or during anticipation to conditional stimulation [Gevins, 1984]. Depending on the experimental paradigm, evoked brain potentials may include a complex of partially overlapping components, reflecting different processing stages along the neural pathways. The concept of a component is related to neural population of specific localization and electric orientation which becomes active during the performance of specific processing.

Two major problems are encountered in analyzing evoked brain potentials: the first stems from the extremely low signal to noise ratio with overlapping spectra of the evoked responses embedded within the background EEG brain activity, ranging from about 0 dB to −20 dB, depending on the type of evoked signals; the second problem concerns possible vectorial signal summation, resulting in componental overlap, which may cause partial or total occlusion of the desired component features. Most of the recently suggested single-trial extraction approaches assume deterministic responses and practically ignore the well-established notion that 'stationary' evoked potentials may be highly variable [e.g. Popivanov & Krekule, 1983], depending on the external experimental conditions as well as on the subject's performance and state of mind [e.g. Michalewski et. al., 1986; Schwent & Hillyard, 1975].

Traditionally, evoked potentials are synchronously averaged to enhance the evoked signal and suppress the background brain activity. Obviously, averaging techniques are in conflict with the attempts to monitor rapid changes of evoked potentials, e.g. during movements with changing loads. Several single-trial estimation techniques were developed during the last decade, usually limited to waveforms similar to the average response, differing only in global latency or scale parameters [e.g. Spreckelsen & Bromm, 1988]. Other techniques were reported as capable of extracting morphologically variable evoked potentials, displaying some experimental results to demonstrate the performance [e.g. Cerutti at. al., 1988; Lange & Inbar, 1996a]; yet none of these methods have demonstrated tracking capabilities of specific components of the evoked potential complex. Thus a new approach to the single-trial EP estimation problem is required.

1.4 Proposed Approach

In evaluating the problem, it would appear that any modeling attempt of evoked potential variability would have to deal with the concept of components, which are the essence of variability analysis in the field of evoked potential research. This called for a definition of an EP component, while considering the fact that evoked potentials may not be decomposed without using constraints to overcome the ill posed inverse problem separation task. Any useful decomposition technique should provide a reasonable representation of the specific signal components which tend to vary in correlation with the variable experimental conditions, so that dynamic brain processes could be followed and tracked.

In readily available EEG recordings the global brain activity obscures the relatively weak evoked signals, and thus methods which utilize the (dis)similarities of a recorded ensemble must be used for the decomposition. In parallel, single-trial estimation methods capable of adequate performance under the low SNR conditions, and incorporating the insight gained by decomposition, are to be developed in order to facilitate variability tracking of single evoked potentials on a trial-to-trial basis. Approaching the problem stage by stage, I developed three serial processing blocks: a self organizing pattern identification network, a statistical decomposition unit, and a parametric synthesis model, which layer by layer uncover the faint brain responses embedded within the ongoing cerebral activity.

Each processing layer can operate independently, as demonstrated below; however using the novel approach, combining unsupervised learning via a competitive neural network with statistical analysis of the spontaneously identified signal patterns and parametric modeling of the signal and noise, the decomposition and single-trial estimation problems are mutually solved to create a unified comprehensive framework for the analysis of transient, trial-varying evoked brain responses.

BRIEF SUMMARY OF THE INVENTION

According to a broad aspect of the present invention, there is provided a method of processing a composite signal generated by a transient generation mechanism to extract a repetitive, low SNR transient signal from noise therein: (a) dynamically identifying, via a learning process, the major transient signal types in the composite signal; (b) decomposing the identified major transient signal types into their respective constituent components; (c) sunthesizing a parametric model emulating the transient signal generation mechanism; and (d) utilizing the model and the constituent components to identify and extract the low SNR transient signal from the composite signal.

According to further features in the preferred embodiment of the invention described below, process (a) is performed by using an adaptive, competitive neural network. More particularly, the neural network includes a group of artificial neurons divided into sets of inhibitory clusters in which all neurons within a cluster inhibit all other neurons in the cluster, resulting in a competition among the neurons in a cluster to respond to the major transient signal patterns in the composite signal.

One application of the invention is described below for identifying and extracting low, evoked-potential (EP) signals appearing in an electroencephalogram (EEG) of a living being generated in response to sensory stimulation of the nervous system of the living being.

According to another aspect of the present invention, there is provided apparatus for processing composite signal in accordance with the above method.

In the described preferred embodiments, the method and apparatus are implemented by computer software, but it will be appreciated that such method and apparatus could be implemented, wholly or partly, also by computer hardware.

Further features and advantages of the invention will be apparent from the description below.

BRIEF DESCRIPTION OF THE DRAWINGS

The invention is more particularly described below with reference to the accompanying drawings, wherein.

2 Review of EP Processing Methods

2.1 Introduction

Figure 1:
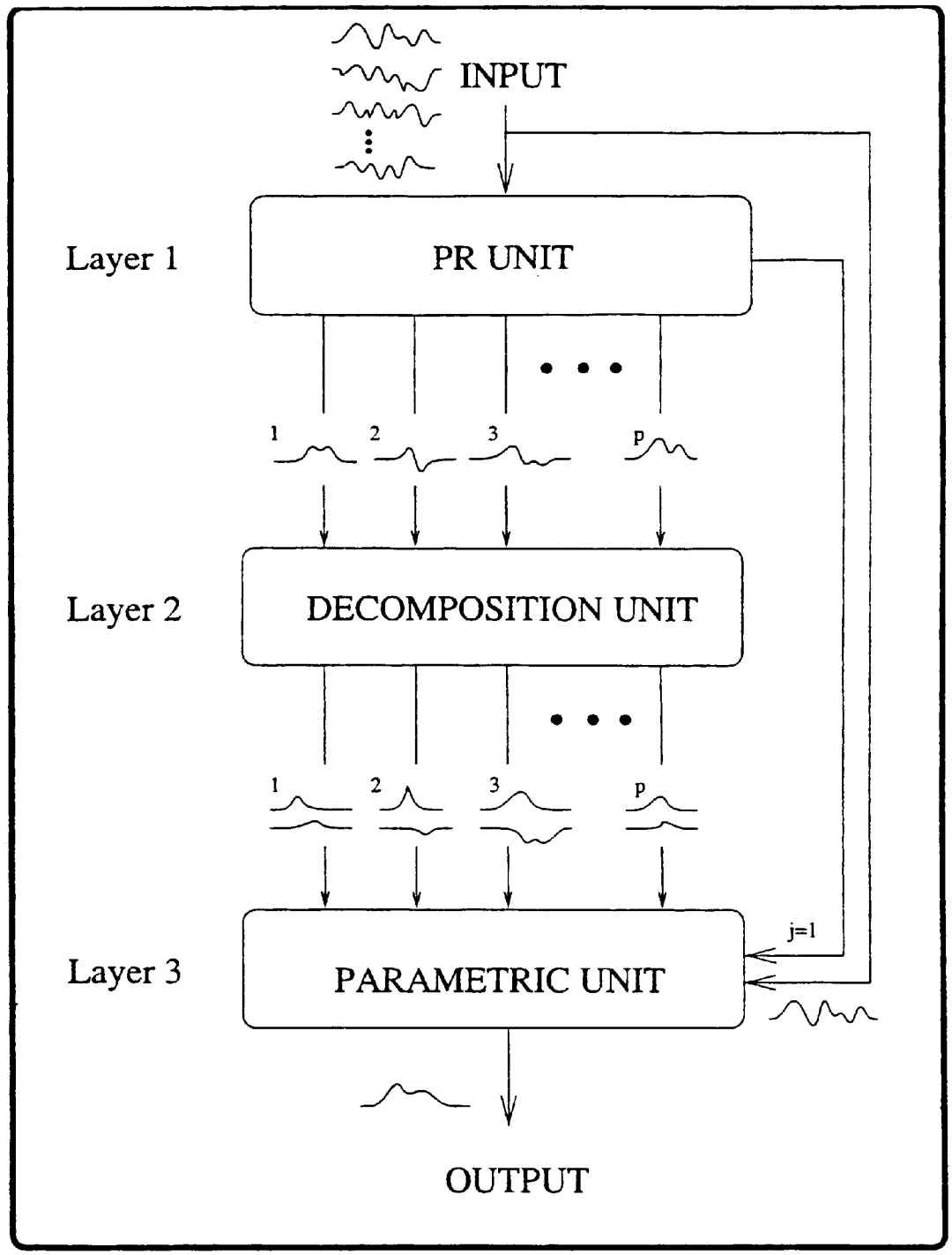
FIG. 1 is a detailed flow chart of the extraction process according to the present invention.

Evoked potential estimation and classification have been sporadically dealt with in Biomedical Engineering literature. Most publications have addressed the issue of improving the signal to noise ratio of the averaged response rather than extraction of single brain responses, probably due to the objective difficulty of analyzing the faint evoked responses embedded within the spontaneous cerebral activity. In order to fully appreciate the contribution of this work to the field of EP estimation, it would be advantageous to first review the historical development of EP processing. A representative summary of common as well as modern EP processing methods follows.

2.2 Processing Methods

Averaging Methods

Ensemble averaging is the traditional and most common method for EP analysis [Rompelman & Ros, 1986a]. In spite of its well known limitations, including but not limited to the inability to estimate trial-varying responses [Rompelman & Ross, 1986b], quite surprisingly averaging is still the most popular EP analysis method. The reasons for this apparent conservatism may vary—from the simplicity of averaging and the consistent results it produces, via limited technical resources of neurophysiologists to apply and assess complicated processing methods, and to the questionable cost-benefit value in using the more advanced methods.

The first attempt to relax the invariant time-locked signal constraint was based on cross-correlation averaging to compensate for latency variation jitter of the evoked responses [Woody, 1967]; the single responses are re-aligned according to cross-correlation measures and improved templates can be obtained. However cross-correlation methods are highly sensitive to the fall of SNR, breaking down for SNR's lower than around 0 dB. In addition, this method does not compensate for changes in response morphology which limits the analysis of variable responses. Cross-correlation averaging was later expanded to allow shifts of single components, however this made the analysis even more sensitive to low SNR's and produced irregularities due to the artificial breaking of the signal into components. Consequently, several latency correction procedures have been proposed, among the recent ones are described in [Gupta et. al., 1996; Kaipio & Karjalainen, 1997; Kong & Thakor, 1996; Meste & Rix, 1996; Nakamura, 1993; Rodriguez, 1981].

Finally, several classification methods have been recently proposed, however none of them is able to identify the embedded signals but only to categorize the recorded data [e.g. Clarson & Liang, 1987; Gevins et. al., 1986; Moser & Aunon, 1986].

Filtering Methods

The first SNR improvement technique that was proposed for EP enhancement applied Wiener filtering to averaged EP's, by calculating filter coefficients from the averaged spectra and the spectrum of the averaged response [Walter, 1969; Doyle, 1975]:

$$H_N(w) = \frac{\phi_{ss}(w)}{\phi_{ss}(w) + \frac{1}{N} \cdot \phi_{xx}(w)} \quad (1)$$

where $\phi_{ss}$, $\phi_{xx}$ are the spectral density functions of the signal and noise, respectively; N accounts for the number of trials used in the averaging process. The motivation to use a-posteriori filtering is due to the multidimensional nature of EP estimation; rather than estimating a noisy scalar signal, where the average may well be the maximum likelihood estimate (e.g. with Gaussian noise), it may be possible to improve beyond averaging due to the coherence of the estimated waveform. Yet the success has been controversial mainly due to the inherent difficulty of spectral estimation of the transient responses [Karlton & Katz, 1987]. A time-varying a-posteriori Wiener filtering structure was also suggested, whose performance was shown to be superior to time-invariant filtering [Yu & McGillem, 1983]. The time-varying Wiener filter was enhanced by using a constant relative bandwidth filters, followed by time-varying attenuators and a summing network controlled by a time-varying SNR estimator in the corresponding frequency bands [de Weerd, 1981]. Other a-posteriori methods have also been developed [Furst & Blau, 1991], yielding similar improvements to those obtained with Wiener filtering.

Thakor has introduced the concept of adaptive filtering to steady-state EP's [Thakor, 1987], providing some improvement in tracking capabilities with respect to averaging techniques. Several adaptive algorithms have evolved from the latter approach, concerned with outperforming averaging in tracking changes of steady state EP's [e.g. Laguna et. al., 1992; Svensson, 1993; Thakor et. al., 1993; Vaz & Thakor, 1989]. These adaptive methods do not apply however to the analysis of transient EP's.

Parametric Methods

The first attempt to extract transient evoked potentials on a single-trial basis, utilyzed an ARX model with the average response driving the exogenous input [Cerutti et. al., 1987]. The basic idea was using the averaged response as a model for the single response, extracted via identification of the model parameters. Elimination of eye-movement artifacts was also incorporated using a similar model [Cerutti et. al., 1988], which was used later for topographic mapping of multi-channel single-sweep brain responses [Liberati et. al., 1992]. There is however a theoretical problem with the ARX model when used for EP extraction; the basic assumption claiming that a single response can be filtered out from the averaged response, by means of linear time invariant (LTI) filtering, is unrealistic due to the trial-varying nature of the evoked responses. In addition, the autoregressive component which represents the ongoing EEG is imposed on the exogenous part, which prevents optimal solution of the EP filter. The empirical results reported were negative in the sense that no correlation was found between the extracted single-trial EP's and experimental manipulation, which may partly be explained by the large estimation variance expected under low SNR conditions. An improvement to the ARX estimator was recently proposed, enhancing the conditions for the EP filter identification and increasing robustness to the strong ongoing activity [Lange, 1994; Lange & Inbar, 1996a].

A different parametric model for single-trial EP extraction was proposed at almost the same time [Spreckelsen & Bromm, 1988], which used AR modeling for the EEG and an impulse response model of a linear system for the EP. The average response was used as the filter impulse response, allowing for amplitude and latency variations of each single-trial response with respect to the averaged response. The reported empirical results presented some correlation between the extracted single EP's and the experimental manipulation, which included global EP decrease due to the administration of a tranquilizer to reduce pain sensation. Finer morphological changes were not reported.

Other Methods

Evoked potential reconstruction by means of a Wavelet transform was recently proposed [Bartnik et. al., 1992]. The principle was to compare the wavelet representation of pre and post-stimulus intervals, and use the differentiating coefficients for reconstruction of the additive EP contribution. The principle underlying this approach is not new and was already investigated previously [e.g. Madhaven, 1992]. However, the proposed implementation is novel, based on decomposing the noisy signals via decreasing scale. The process is comparable to taking a picture from increasing distances by a factor of $\alpha$; on the j-th step the resolution decreases by a factor of $\alpha^j$, where the picture of $\alpha^j$ resolution can be restored from the higher detailed picture of $\alpha^{j+1}$ resolution. The algorithm projects the background activity of the pre- and post-stimulus signals onto an orthonormal basis derived from a Wavelet function, finds the principal basis components which best differentiate the two projections, from which it constructs the single response. A major problem lies in identifying the optimal scaling function $\phi(x) = \alpha^j \phi(\alpha^j x)$ to fit the signals at hand, and a direct use of the average response is necessary to determine $\phi(x)$. A primary theoretical drawback is the critical assumption that any irregularities during the epoch must be related to the specific time-locked task. This is unlikely due to the wide-sense definition of an EP, as well as due to other various reasons like EMG artifacts or EEG irregularities. The reported empirical results are hard to evaluate because identical stimuli were used yet large estimation variances were obtained.

Single-trial extraction using statistical outlier identification has also been attempted [Birch et. al., 1993], generalized later to extraction of low SNR events [Mason et. al., 1994]. The outlier processing method was based on building an AR model whose parameters represent the underlying ongoing EEG process. The model was identified by using a robust parameter estimation method, which suppressed non conforming activity during the model building process. Then, the model was used to reconstruct the ongoing EEG, where its difference from the measured process was considered to be the additive outlier content. The method's advantage lies in its minimal assumption about the signal, requiring only for it to last no longer than about 20% of the entire epoch. As the percentage increases, so do the inaccuracies due to the AR model builder sensitivity to outlier contamination of the EEG. This method suffers from the same theoretical drawback as the previous approach, due to the inherent variability of the EEG signal. The experimental results, dealing with Movement Related Potentials, demonstrate some uniformity in the resulting waveforms across subjects and movements. Yet the variance is high, probably due to irrelevant statistical outlier disturbances.

Current State of EP Analysis

Current single-trial extraction methods may generally be divided into two main categories. The first includes template-based LTI models, displaying some success with constant responses (e.g. brain-stem signals), as well as with variability of global magnitude and/or phase of the evoked responses. The second category includes methods which attempt to reconstruct the EP by means of identification of statistical changes of the EEG signal over the transition from pre-stimulus to post-stimulus interval; these methods suffer from high estimation variances, probably due to physiological signal contamination of the background EEG.

Generally a tendency towards parametric techniques is observed, as spectral methods are inadequate to deal with the spectral overlap of the EP and EEG at the unfavorable SNR characteristic of EP signals. To date, no serious attempt has been made to track variability of evoked potential components on a trial-to-trial basis, as most of the contributions focus on extracting average-like waveforms from single-trial recordings. Thus a need for more sensitive methods which can extract trial-varying responses is evident.

DETAILED DESCRIPTION OF THE PRESENT INVENTION

3 Outline and Scope

The description below presents a comprehensive framework for transient EP processing on a single-trial basis. This chapter outlines my perspective of the single-trial processing problem and its difficulties, gives a critical presentation of the common assumptions and approaches used in EP analysis, presents a summary of the contributions presented in the following chapters along with outlining the organization of the description, and then sets a new approach to solving this problem.

3.1 Conventional EP Processing

When using the term evoked potential one usually refers to the average evoked response, obtained via averaging many synchronized brain responses time-locked to a repeating stimulus or event. The single evoked response has not been useful since it is embedded deep within massive background brain activity. Conventional EP processing relies on several major assumptions, whose validity may depend on factors related to the experimental paradigm as well as to the subject's state of mind:
1) A repetitive, invariable time-locked signal (EP)
2) Additivity of signal and noise
3) A stochastic, stationary noise (EEG)
4) Uncorrelated signal and noise The first assumption is generally not valid, except in some special cases, and is often the source of error in many template-based processing methods which rely heavily on the average response as a template for analysis. Examples of EP variability are numerous—the responses are known to be influenced by the mental state of the subject, fatigue, habituation, level of attention, quality of performance, and so on. This assumption, which is considered to be the main drawback of most EP processing methods, is battled throughout this work.

The second assumption, which is more of a convention, states that the evoked response is added to the background activity without affecting it, so that any part of the response that is influenced by the stimulus is incorporated in the EP. This is a common assumption underlying almost all EP analysis frameworks, adopted also in this work.

The third assumption means that the spontaneous EEG is uncorrelated over long time periods; it is easily verifiable by EEG correlograms demonstrating the uncorrelation for periods in the order of 1–2 seconds, and is therefore adopted in this work.

The fourth assumption is essential for methods based on correlation, as phase matches of EEG and EP would give rise to errors in estimating single EP waveforms. However it should be noted that, by definition, the sum of all EEG components which are correlated with the stimulus are regarded as the EP, making it more of a definition than as assumption. This assumptions is also adopted in this work.

Based on the above assumptions, various EP processing methods have been proposed, ranging from simple latency-correcting and spectral filtering algorithms to sophisticated single-trial methods. Yet due to insufficient exposure to clinicians such methods have not been thoroughly evaluated, and conventional averaging is still the most common method in EP analysis. It may be that due to the wide usage of the EP invariability assumption, the added value of using recent advanced techniques becomes questionable and thus a major relaxation of this assumption is required.

3.2 Proposed Framework

The proposed framework consists of three data-driven serial layers (FIG. 1): (1) a pattern identification layer, consisting of an unsupervised identification mechanism, (2) a statistical decomposition layer, consisting of a linear decomposition unit, and (3) a parametric synthesis unit based on the additivity of the EEG and EP contributions. A thorough description, analysis, and performance evaluation of each layer is given in the following chapters. The purpose of this outline is to elucidate the logic behind the approach, and to clarify the structure and scope of the proposed framework, which can be summarized as follows:

- The first layer consists of an unsupervised learning structure in the form of a competitive artificial neural network, which is used to dynamically identify the various response types embedded within the recorded ensemble. The constraint of this layer lies in the assumption that the single brain responses are not randomly distributed, but rather belong to a relatively small family of brain responses. Identifying the waveform family, the network spontaneously builds a library of the embedded data types. The logic behind the underlying assumption of categorizable brain responses is based on the expected consistency of brain function, which is at the core of brain signal analysis; if the responses were random then it would not be possible to correlate them to the experimental paradigm and our efforts would be in vain. The proposed structure is tested with simulations as well as with real biological data, providing reproducible high quality identifications.

- The second layer consists of a linear statistical decomposition scheme, responsible for separation of the identified library items into constituent components. The purpose of decomposition is to allow certain variability of each response with relation to its respective library item, and thus to enable tracking of trial-to-trial variability of the evoked responses. An additional assumption employed has to do with the statistical nature of cortical neural activity; Gaussian distributions are used to model the firing instants of a synchronously activated ensemble of cortical neurons. As the true neural activation characteristics is obviously unknown, and any assumption regarding the statistics of cortical neural activation might be severely violated, a robust method which does not inflict significant distortions on the separated signal components is used. The proposed method is tested with simulations as well as with biological data, resulting in adequate decompositions fitting the simulated components, while justifiable components were obtained in the case of overlapping EP data.

- The third and final layer consists of a parametric synthesis model, emulating the single-sweep signal generation mechanism. Dealing with low SNR signals, the model relies on preliminary information extracted via the previous processing layers, utilizing the identified EP waveform types. Once its parameters are identified, the model successfully generates the single-sweep recording from its assumed contributions—the EEG and EP, where the identified EP is the desired output of the integrated system. The parametric model is evaluated analytically and via simulations, substantiating its high performance as presented with real EP data.

3.3 Organization of Description

The next chapter (4) deals with unsupervised learning and its applicability to the EP estimation problem. It starts with the essentials of unsupervised learning and focuses on a competitive learning neural network and its unique advantage as a signal identification network. The competitive network is shown to encapsulate the embedded signal characteristics in a small set of library items, used in the following signal extraction stages. The network performance is analyzed from an information theoretic perspective, followed by a simulation study whose results match the analytical observations. Finally application to real-life EP data is demonstrated.

Chapter 5 discusses issues related to coherent brain activity, and presents a statistical approach for decomposition of brain signals into constituent components. The approach is simple yet robust and provides lossless decomposition of each library item into a set of constituent components. The decomposed waveforms are used for variability analysis of each evoked response related to a specific library item. A simulation study demonstrates robustness of the decomposition scheme to violations of the assumptions, substantiating its use for EP decomposition. Finally, decomposition examples of real-life EP data are presented.

Chapter 6 presents the parametric synthesis model, responsible for synthesizing the measured noisy sweep via emulating its two assumed constituents: the background EEG and single-trial EP. The estimation performance is analyzed analytically, followed by a simulation study confirming the estimation capabilities. Ultimately the parametric model is tested with real-life evoked potential data, demonstrating its utility in tracking EP components and waveforms on a single-trial basis.

The dissertation closes with a summary, discussion, and propositions for further research, and supplemented with extended graphical results and some complementary material.

4 Pattern Identification of EP's

4.1 Introduction

Investigation of brain function via EP analysis assumes that coherent neural processes are manifested in the electrical activity of the brain measured from the scalp. It must be further assumed that consistency of the brain electrical activity is maintained, in the sense that variations of the evoked responses may be attributed to changes in the underlying physiological mechanisms. When attempting to estimate the evoked responses from noisy brainwave recordings, due to the extremely low signal to noise ratio, as much information as possible regarding the signal and noise must be considered.

The first stage of analysis is responsible for the extraction of a basic library of evoked responses, specific to the subject, which would serve as a first approximation or template to the following signal decomposition and modeling procedures. An unsupervised learning pattern identification structure is used in order to objectively identify the embedded response types or categories, making use of the partial correlations of the ensembled data sets.

4.2 Problem Statement

The major problem lies in the extremely unfavorable SNR of the evoked responses embedded within the ongoing background brain activity. Classification and estimation of the single evoked responses are thus difficult tasks, complicated further due to non-stationarities of the signal and noise. A common assumption among most researchers is that the measured waveform is the sum of a signal component (EP) and a statistically independent noise component (EEG) [Gevins, 1984]. This is more of a definition than an assumption, since it is only natural to define the signal as the component which is correlated with the applied stimulus. It should be noted that a different hypothesis was also proposed, referring to the phase spectrum of the post-stimulus EEG; while such phase values are random at the absence of stimulus, aggregated phase values appear with repeating stimulus presentation [Beagly et. al., 1979]. In practice, however, identical stimuli do not necessarily evoke identical responses. Trial-to-trial variability can be substantial, and EP waveform, amplitude, and latency can change abruptly or progressively in time. Thus, the basic assumption underlying signal averaging and spectral analysis is generally violated.

The complicated, generally unknown relationships between the stimulus and its associated brain response, and the extremely low SNR of the brain responses which are practically masked by the background brain activity, make the choice of a self organizing structure for post-stimulus epoch analysis most appropriate. The competitive network, implemented so that its weights converge to the actual embedded signal waveforms while inherently averaging out the additive background LEG, is thus an evident choice [Lange et. al., 1998].

4.3 Unsupervised Learning
4.3.1 Self Organization

Machine learning can be implemented my means of a dynamic neural structure, which has an ability to learn from its environment, and through learning to improve its own performance. Unsupervised learning, in the form of a self organizing neural structure, is used to discover significant patterns or features in the input data, through a spontaneous learning paradigm. To achieve such spontaneous learning, the algorithm is equipped with a set of rules of a local nature, which enable it to learn its environment via some sort of mapping with specific desirable properties [Duda & Hart, 1976].

The learning process is based on positive feedback or self re-enforcement, stabilized by means of a fundamental rule: an increase in strength of some synapses in the network must be compensated for by a decrease in other synapses. In other words, a competition takes place for some limited resources, preventing the system from exploding due to the positive feedback based learning process. I have chosen to use a competitive neural network structure, which will be shown to possess important features rendering its application as an Identification Network of the low SNR transient brain signals.

4.3.2 Competitive Learning

Competitive learning is an established branch of the general theme of unsupervised learning. The elementary principles of competitive learning are [Rumelhart & Zipser, 1985]:

Start with a set of units that are all the same except for some randomly distributed parameter which makes each of them respond slightly differently to a set of input patterns.

Limit the 'strength' of each unit.

Allow the units to compete in some way for the right to respond to a given subset of inputs.

Applying these three principles yields a learning paradigm in which individual units learn to specialize on sets of similar patterns and thus become 'feature detectors'. Competitive learning is a mechanism well-suited for regularity detection [Haykin, 1994], where there is a population of stimulus patterns each of which is presented with some probability. The detector is supposed to discover statistically salient features of the input population, without requiring an a-priori set of categories into which the patterns should be classified. Thus the detector needs to develop its own featural representation of the population of input patterns capturing its most salient features.

Finally, it is worth noting that competitive representations have some generic disadvantages over distributed representations [Hertz at. al., 1991]: they need one output neuron for each category, thus N neurons can model only N categories compared to $2^N$ for a binary code; they are not robust to neuron failure, which would cause loss of the whole respective category; and they cannot represent hierarchical knowledge—there is no way to have categories within categories (unless the winner takes all principle is relaxed).

4.4 The Competitive Neural Network Structure
4.4.1 Theory

Figure 2:
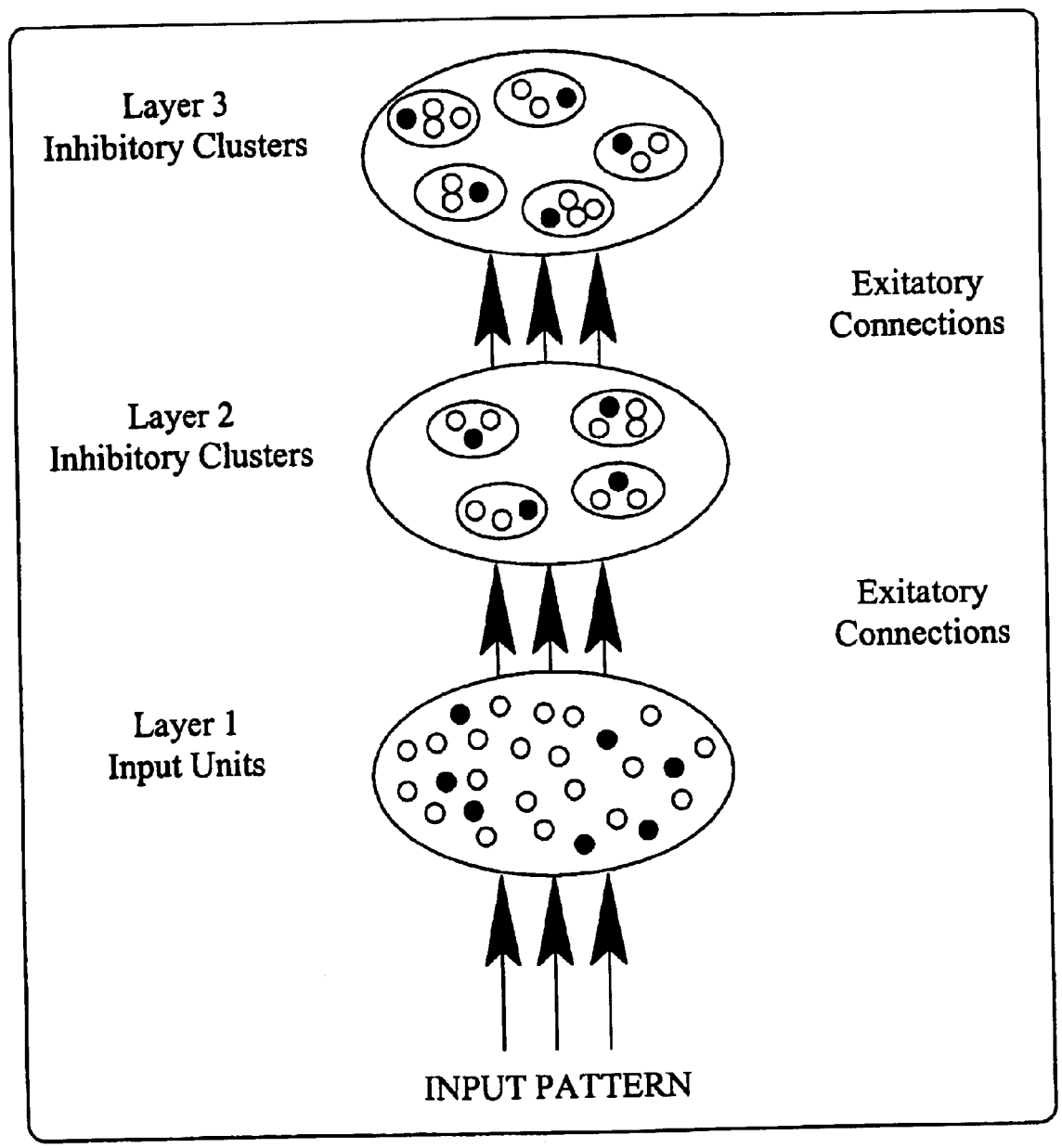
FIG. 2 illustrates the architecture of a competitive learning structure performed by layer 1 of FIG. 1.

A typical architecture of a competitive learning system appears in FIG. 2. The system consists of a set of hierarchically layered neurons in which each layer is connected via excitatory connections to the following layer. Within a layer, the neurons are divided into sets of inhibitory clusters in which all neurons within a cluster inhibit all other neurons in the cluster, resulting in a competition among the neurons to respond to the pattern appearing on the previous layer; the stronger a neuron responds to an input pattern, the more it inhibits the other neurons of its cluster.

Figure 3:
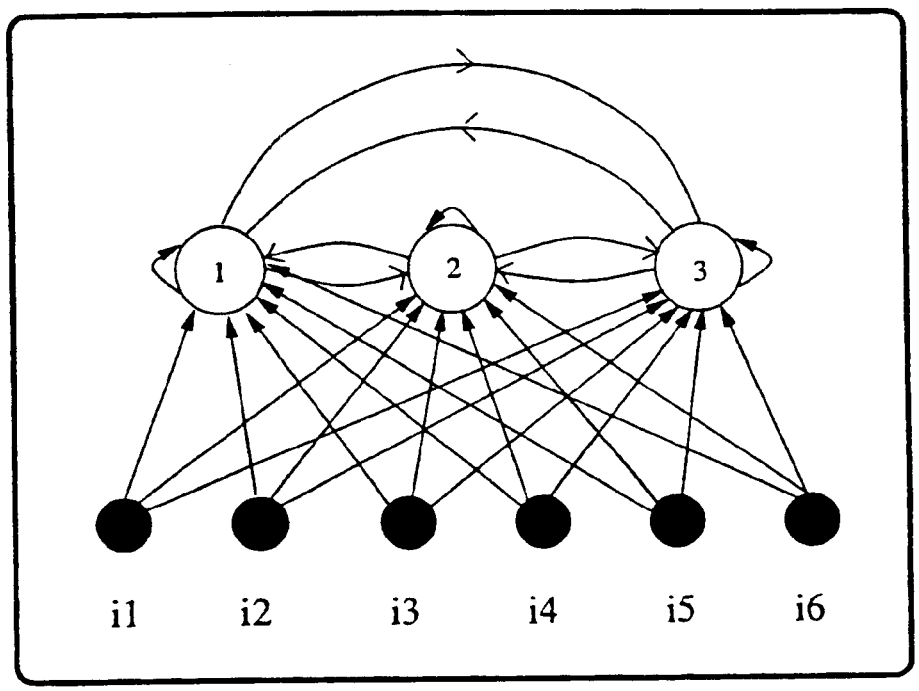
FIG. 3 illustrates a single-layer competitive learning process performed by the structure of FIG. 2.

There are many variations of the competitive learning scheme. I have selected a single layer structure, where the output neurons are fully connected to the input nodes and the non-linearity is implemented in the learning-phase only. The advantage of using this structure lies in enhanced analysis capabilities of the converged network, as the weights actually converge to the embedded signal patterns and thus form a Pattern Identification network. The general network structure is depicted in FIG. 3. For neuron j to be the winning neuron, its net internal activity level $v_j$ for a specified input pattern $x_i$ must be the largest among all neurons in the network. The output signal $y_j$ of a winning neuron j is set equal to one, and all other neuron outputs that lose the competition are set equal to zero.

Let $w_{ji}$ denote the synaptic weight connecting input node i to neuron j. Each neuron is given a fixed amount of synaptic energy, which is distributed among its input nodes:

$$\sum_i w_{ji}^2 = 1, \text{ for all } j \tag{2}$$

Figure 4:
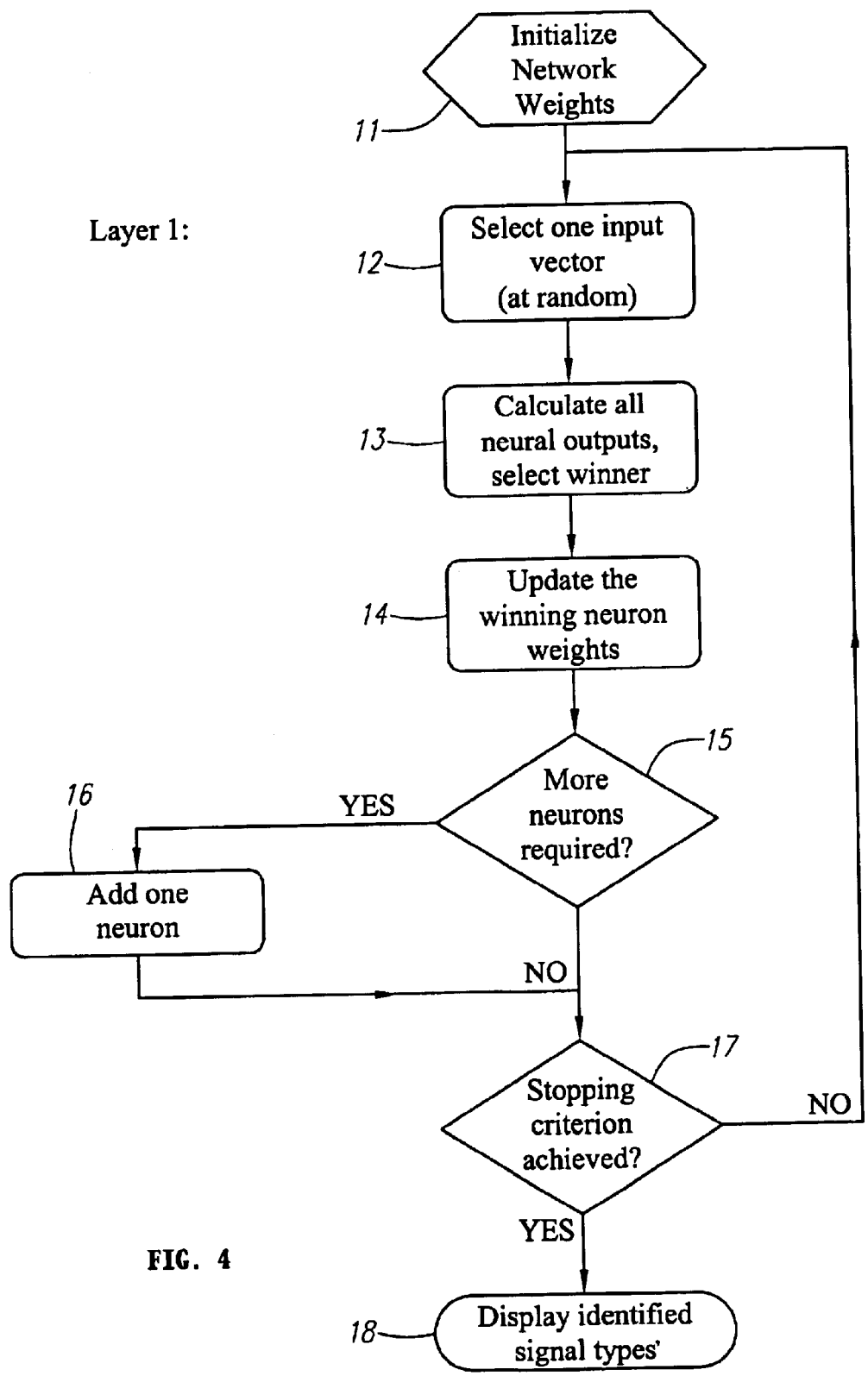
FIG. 4 is a flow chart illustrating the learning process performed by layer 1 in FIG. 1.

A neuron learns by shifting synaptic weights from its inactive to active input nodes. If a neuron does not respond to some input pattern, no learning occurs in that neuron. When a single neuron wins the competition, each of its input nodes give up some proportion of its synaptic weight, which is distributed equally among the active input nodes. According to the standard competitive learning rule, for a winning neuron, the change $\Delta w_{ji}$ applied to synaptic weight $w_{ji}$ is defined by:

$$\Delta w_{ji} = \eta(x_i - w_{ji}) \quad (3)$$

where $\eta$ is the learning rate coefficient. The effect of this rule is that the synaptic weight of a winning neuron is shifted towards the input pattern. In our case, where the signals are assumed to be embedded within an additive Gaussian noise, the network weight structure converges to a matched filter bank, operating as a pattern identification network as well as an optimal signal classifier. The foregoing operations are indicated by blocks 11–18 in the flow chart of FIG. 4.

A common problem with random initialized competitive artificial neural networks (ANN) is the phenomenon of stuck vectors. The training process may result, in extreme cases, in all weight vectors but one becoming stuck, sometimes also referred to as dead neurons; a single weight vector may always win and the network would not learn to distinguish between any of the classes. This happens because of two reasons [Freeman & Skapura, 1992]: first, in a high dimensional space, random vectors are all nearly orthogonal, and second, all input vectors may be clustered within a single region of the space. A known solution for this problem is to include a variable bias, in the form of a time-constant, giving advantage to neurons which rarely or never win over neurons which always win. The bias of a dying neuron is increased proportionally to the number of winnings of the other neurons, and decreased after it gains victory over the other neurons to allow fair competition. This bias is used during training only and discarded thereafter.

4.4.2 Model and Assumptions

Before presenting in detail the competitive ANN structure, the assumed model needs to be described. I shall start with the model assumptions:

1. The EEG and EP are additively superpositioned in the recorded sweeps.
2. The background EEG is uncorrelated across sweeps.
3. The EEG and EP are uncorrelated.
4. The dimension of signal space is substantially smaller than the dimension of the input space; that is, there are fewer EP types than number of noisy input sweeps. Within each type, the signal variability is small.

Assumptions 1–3 are conventional, and have to do with the definition of EEG and EP as presented in the introduction. Assumption 4 replaces the common restrictive assumption of response invariability, and permits existence of more than one typical EP waveform in an experimental session. Limiting within-class or within-type signal variability is necessary to ensure that within-class variability is small compared to cross-class variability; yet modeling of within-class variability is not ignored and is implemented in following processing stages.

The above assumptions, along with the desire for real-time applicability, have led to using a competitive neural structure which provides means for identification of the embedded signal types. The implementation can be done on-line, identifying signal types as the experimental session is progressing, and is thus suitable for real-time monitoring purposes.

4.4.3 Statistical Evaluation

Identification Property

The essential identification feature of the proposed network is, ideally, an inherent convergence of the network weights to the embedded EP waveforms, thus operating as a Pattern Identification network. In an optimal scenario, in which the embedded EP patterns and background EEG are uncorrelated, each of the competing neurons tends to fixate on a different signal type by mapping itself to a specific signal waveform. Each single measurement can be represented as follows:

$$x_i(t) = \sqrt{E_i} s_i(t) + e_i(t), \; i=1,2,\ldots,N \quad (4)$$

where $x_i$, $E_i$, $s_i$ and $e_i$ represent the recorded i-th single-sweep, the energy of the i-th EP, the normalized EP waveshape and the embedding background EEG, respectively. Assuming P<N correctly identified signal categories, where $s_i \in \{S_j\}_{j=1}^{P}$, and using normalized inputs and weights and a Gaussian model for the background EEG, it can be shown that in each iteration the winning neuron shifts its weights towards the respective EP pattern. First we calculate the neural outputs:

$$o^k = \langle x_i, w^k \rangle, \; k=1\ldots P$$

Then, selecting the winning neuron l=maxar g{$o^k$}, we update the weights of the winning neuron only:

$$w_n^l = w_{n-1}^l + \eta \cdot (x_i - w_{n-1}^l) \quad (5)$$

The winning neuron's output to a matching single-trial measurement is increasing monotonically (note: $|o^l(\cdot)|<1$):

$$\begin{aligned} o_n^l &= \langle x_i, w_{n-1}^l + \eta \cdot (x_i - w_{n-1}^l) \rangle \\ &= o_{n-1}^l + \langle x_i, \eta \cdot (x_i - w_{n-1}^l) \rangle \\ &= o_{n-1}^l + \eta \cdot \langle x_i, x_i \rangle - \eta \cdot \langle x_i, w_{n-1}^l \rangle \\ &= o_{n-1}^l + \eta \cdot (1 - o_{n-1}^l) \end{aligned} \quad (6)$$

and thus:

$$o_n^l \geq o_{n-1}^l \quad (7)$$

Hence it was shown that matching neurons approach the embedded patterns monotonically, and thus each neuron will finally converge to a respective embedded ERP pattern, yielding a matched filter bank network. The pattern identification procedure is unbiased and the variance could be made as small as desired by decreasing the learning-rate coefficient, as presented in the following sections.

Identification Bias

The competing neurons are mapped to the input space, and the correlation of the neurons' weights with their matching input patterns is ever increasing, i.e. the learning processes of the competing neurons are assumed to be independent. It is thus sufficient to evaluate a single neuron system detecting a constant signal pattern embedded within random noise realizations.

Recalling the competitive learning rule, applied to the winning neuron, we have:

$$w_n = w_{n-1} + \eta \cdot (x_i - w_{n-1}); \; 0 < \eta < 1 \quad (8)$$

where $x_i$ is an arbitrary input vector. Rearranging and using the additive signal and noise model yields:

$$w_n = w_{n-1} \cdot (1-\eta) + \eta \cdot (s + e_i), \quad (9)$$

where s and $e_i$ represent the embedded signal pattern and the embedding noise realizations respectively. This difference equation can be solved as follows:

$$w_n = (1-\eta)^n \cdot w_0 + [(1-\eta)^{n-1} \cdot \eta \cdot (s+e_1) + (1-\eta)^{n-2} \cdot \eta \cdot (s+e_2) + \ldots + \quad (10)$$
$$(1-\eta) \cdot \eta \cdot (s+e_{n-1}) + \eta \cdot (s+e_n)]$$
$$= (1-\eta)^n \cdot w_0 + \eta \cdot \sum_{i=0}^{n-1} (1-\eta)^i \cdot (s+e_{n-i})$$
$$= (1-\eta)^n \cdot w_0 + \eta \cdot s \cdot \sum_{i=0}^{n-1} (1-\eta)^i + \eta \cdot \sum_{i=0}^{n-1} (1-\eta)^i \cdot e_{n-i}$$
$$= (1-\eta)^n \cdot w_0 + s \cdot (1-(1-\eta)^n) + \eta \cdot \sum_{i=0}^{n-1} (1-\eta)^i \cdot e_{n-i}$$

Taking the limit as n approaches infinity, where $0 \leq \eta \leq 1$, $\tilde{e}_i = e_{n-i}$, yields:

$$w_\infty = s + \eta \cdot \sum_{i=0}^{\infty} (1-\eta)^i \cdot \tilde{e}_i \quad (11)$$

and calculating the expectancy provides the unbiased result:

$$E[w_\infty] = s + \eta \cdot \sum_{i=0}^{\infty} (1-\eta)^i \cdot E[\tilde{e}_i] \quad (12)$$

$$E[w_\infty] = s \quad (13)$$

Identification Variance

Assuming zero-mean Gaussian EEG with $\sigma^2$ variance, and recalling the solution of the learning rule equation:

$$w_n = s + \eta \cdot \sum_{i=0}^{n-1} (1-\eta)^i \cdot \tilde{e}_i, \quad (14)$$

we can calculate the identification variance (I denotes the identity matrix):

$$E(w_n - s)(w_n - s)^T = E\left[\left(\eta \cdot \sum_{i=0}^{n-1} (1-\eta)^i \cdot \tilde{e}_i\right)\left(\eta \cdot \sum_{i=0}^{n-1} (1-\eta)^i \cdot \tilde{e}_i^T\right)\right] \quad (15)$$

$$= \eta^2 \cdot \sum_{i=0}^{n-1} \sum_{j=0}^{n-1} (1-\eta)^i (1-\eta)^j \cdot E[\tilde{e}_i \cdot \tilde{e}_j^T]$$

$$= \eta^2 \cdot \sum_{i=0}^{n-1} (1-\eta)^{2i} \cdot \sigma^2 \cdot I$$

$$= \eta^2 \cdot \frac{1-(1-\eta)^{2n}}{1-(1-\eta)^2} \cdot \sigma^2 \cdot I$$

Taking the limit as n approaches infinity yields the asymptotic identification variance:

$$C_{ww} = E(w_\infty - s)(w_\infty - s)^T = \frac{\eta}{2-\eta} \cdot \sigma^2 I \quad (16)$$

Bounding the Learning Rate

Figure 5:
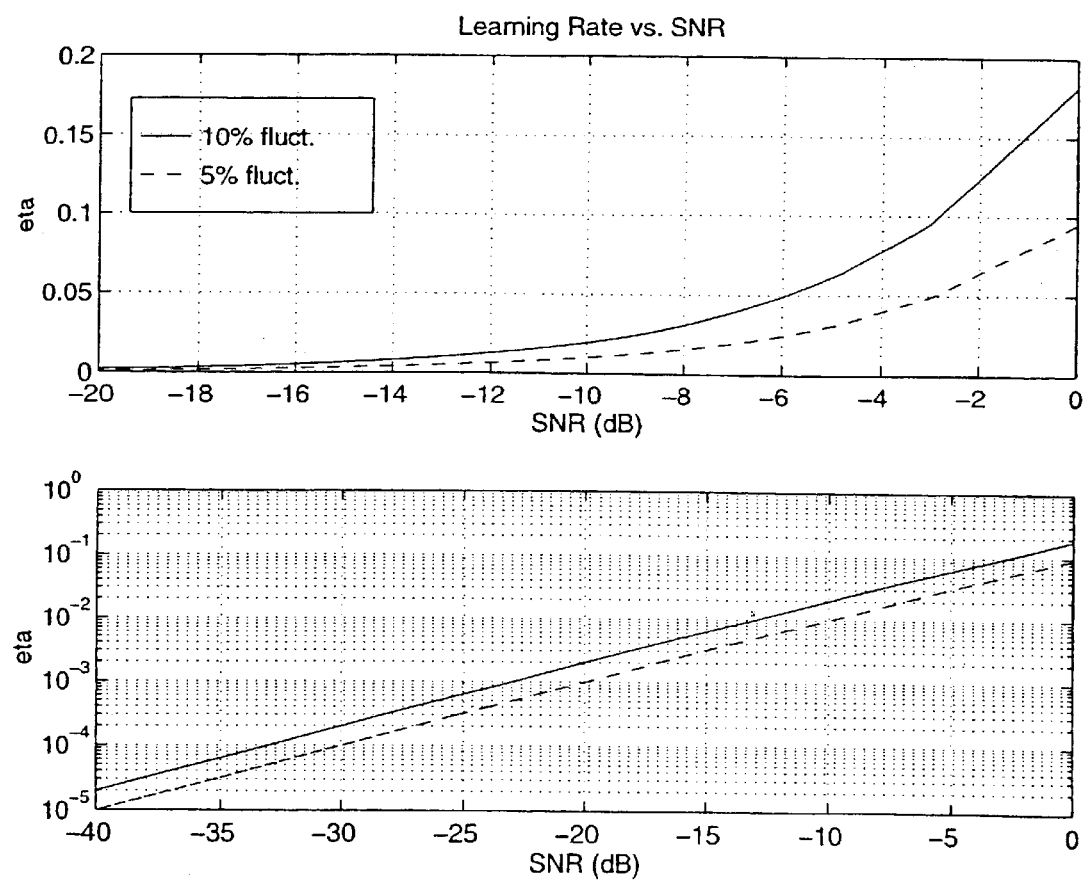
FIG. 5 presents graphical data regarding the learning process of layer 1.

Noting that the weight fluctuations due to the variance of estimation could be limited to ensure that the identified waveforms would not be significantly distorted, it is useful to bound the learning rate coefficient. Requiring $C_{ww} \leq \alpha \cdot E \cdot I$ where $C_{ww}$, $\alpha$ and E are the estimation covariance matrix, the distortion coefficient, and the energy of the signal, yields:

$$\frac{\eta}{2-\eta} \cdot \sigma^2 \leq \alpha \cdot E \quad (17)$$

and solving for $\eta$ provides the bound:

$$\eta \leq \frac{2\alpha \frac{E}{\sigma^2}}{1 + \alpha \frac{E}{\sigma^2}} \quad (18)$$

e.g. for SNR's of 0 dB, −20 dB, and −40 dB, and for a distortion coefficient of $\alpha=0.1$, the learning rate coefficient should not exceed 0.18, 0.0198 and 0.002 respectively. FIG. 5 illustrates the maximun learning rate as a function of the SNR, at noise fluctuation levels of 10% (solid) and 5% (dashed) of the signal energy. The noise fluctuations decrease with lowering of the learning rate, at the expense of an extended learning cycle.

Learning Cycle Duration

The learning process is a non-linear one, and the convergence time depends on several unknown factors like the degree of correlation among the various signal patterns. However it is possible to provide a "thumb rule" for the required learning cycle duration, which may prove useful at least for initial assessment of the data at hand.

Referring to Eq. 11, an exponential envelope of time constant $\tau_\eta$ can be fitted to the geometric series by assuming the unit of time to be the duration of one iteration cycle, and by choosing a time constant $\tau_\eta$ such that:

$$(1-\eta) = \exp\left(-\frac{1}{\tau_\eta}\right). \quad (19)$$

Therefore $\tau_\eta$ can be expressed in terms of the learning rate coefficient $\eta$:

$$\tau_\eta = -\frac{1}{\ln(1-\eta)} \quad (20)$$

The time constant $\tau_\eta$ defines the time required for a decay of the noise contribution to $\frac{1}{e}$ of its initial value, for a single neuron. For multiple neurons, the required learning cycle should be multiplied by the number of competing neurons.

With low SNR EP's, dictating slow learning rates ($\eta <<1$), the time constant $\tau_\eta$ may be approximated by (P denotes the number of competing neurons):

$$\tau_\eta \approx \frac{P}{\eta} \quad (21)$$

4.4.4 Network Training and Convergence

Our net includes a 300-node input layer (equal to input vector dimension), and a competitive layer consisting of single-layered competing neurons. The network weights are initialized with random values and trained with the standard competitive learning rule, applied to the normalized input vectors:

$$\Delta \omega_{ji} = \eta \left( \frac{x_i}{\|x_i\|_2} - \omega_{ji} \right) \quad (22)$$

The training is applied to the winning neuron of each epoch, while decreasing the bias of the frequently winning neuron to gradually reduce its chance of winning consecutively (eliminating the dead neuron effect). Symmetrically, its bias is increased with the winnings of other neurons.

In order to evaluate the network performance, we explore its convergence by analyzing the learning process via the continuously adapting weights:

$$\rho_j(n) = \sqrt{\sum_i (\Delta \omega_{ji})^2} \; ; \; j = 1, 2, \ldots, P \quad (23)$$

where P represents the number of competing neurons (and thus the number of obtained categories). We define a set of classification confidence coefficients of the converged network. Ranging from 0 to 1 (random classification to completely separated categories), the confidence coefficients indicate the reliability of classification which breaks down with the fall of SNR:

$$\Gamma_j = 1 - \frac{\rho_j(N)}{\max_j \{\rho_j(N)\}} \quad (24)$$

4.4.5 Simulation Study

Classification Performance

Figure 6:
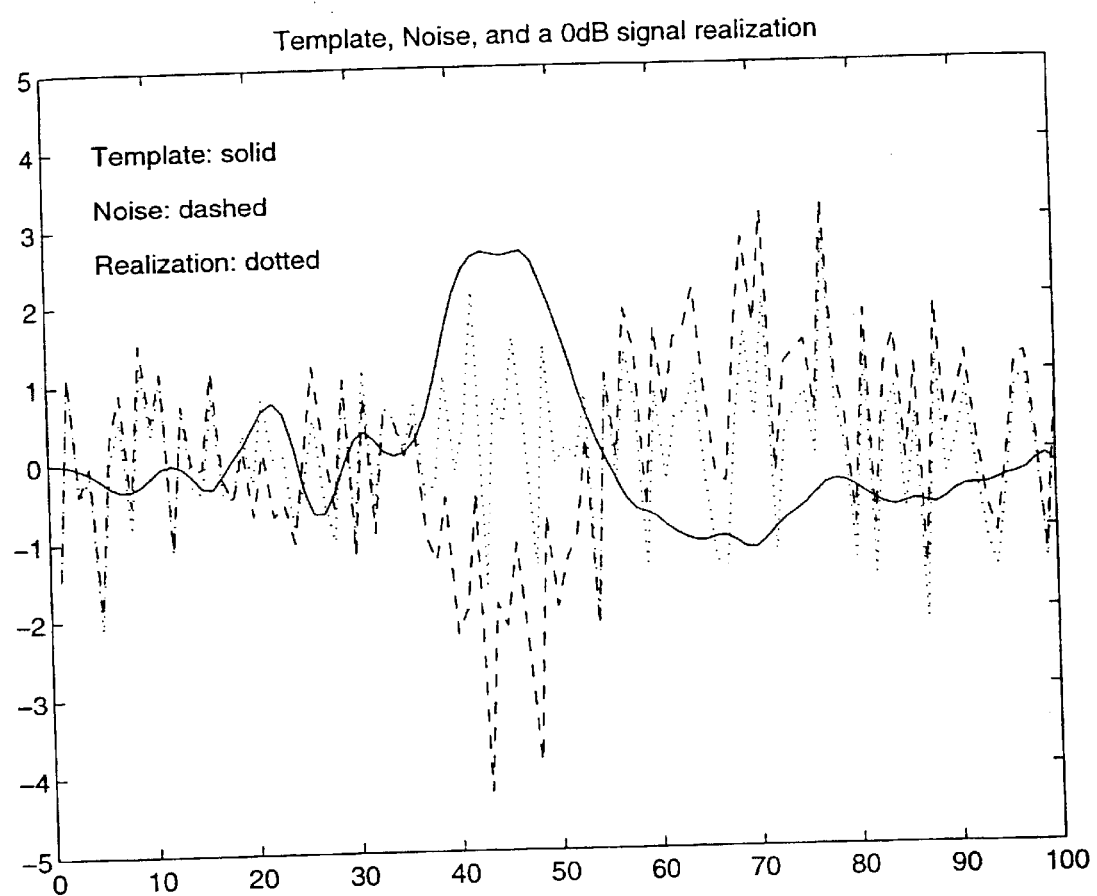
FIG. 6 presents further graphical data regarding the learning process of layer 1.

A computer simulation was carried out to assess the classification performance of the competitive ANN classification system. A moving average process of order 8 selected according to Akaike's condition applied to ongoing EEG [Akaike, 1970; Gersch, 1970], driven by a deterministic realization of a Gaussian white noise series, simulated the ongoing background activity x(n). An average of 40 single-trials from a cognitive odd-ball type experiment (to be explained in the Experimental Study), was used as the signal s(n). Then, five 100-trial ensembles were synthesized, to study the network performance under variable SNR conditions. A sample realization and its constituents, at an SNR of 0 dB, is shown in FIG. 6.

The simulation included embedding the signal s(n) in the synthesized background activity x(n) at five SNR levels (−20, −10, 0, +10, and +20 dB), and training the network with 750 sweeps (per SNR level). Table 1 below illustrates the classification results for the variable SNR's, wherein it is seen that, consistent with the previous findings, the classification performance degrades with the fall of SNR towards −20 dB.

TABLE 1

Classification results for variable SNR's. Consistent with the previous findings, the classification performance degrades with the fall of SNR towards −20 dB.

| | Pos | Neg | FP | FN |
| --- | --- | --- | --- | --- |
| snr = +20 dB | 100% | 100% | 0% | 0% |
| snr = +10 dB | 100% | 100% | 0% | 0% |
| snr = 0 dB | 100% | 100% | 0% | 0% |
| snr = −10 dB | 88% | 92% | 8% | 12% |
| snr = −20 dB | 58% | 54% | 46% | 42% |

Figure 7:
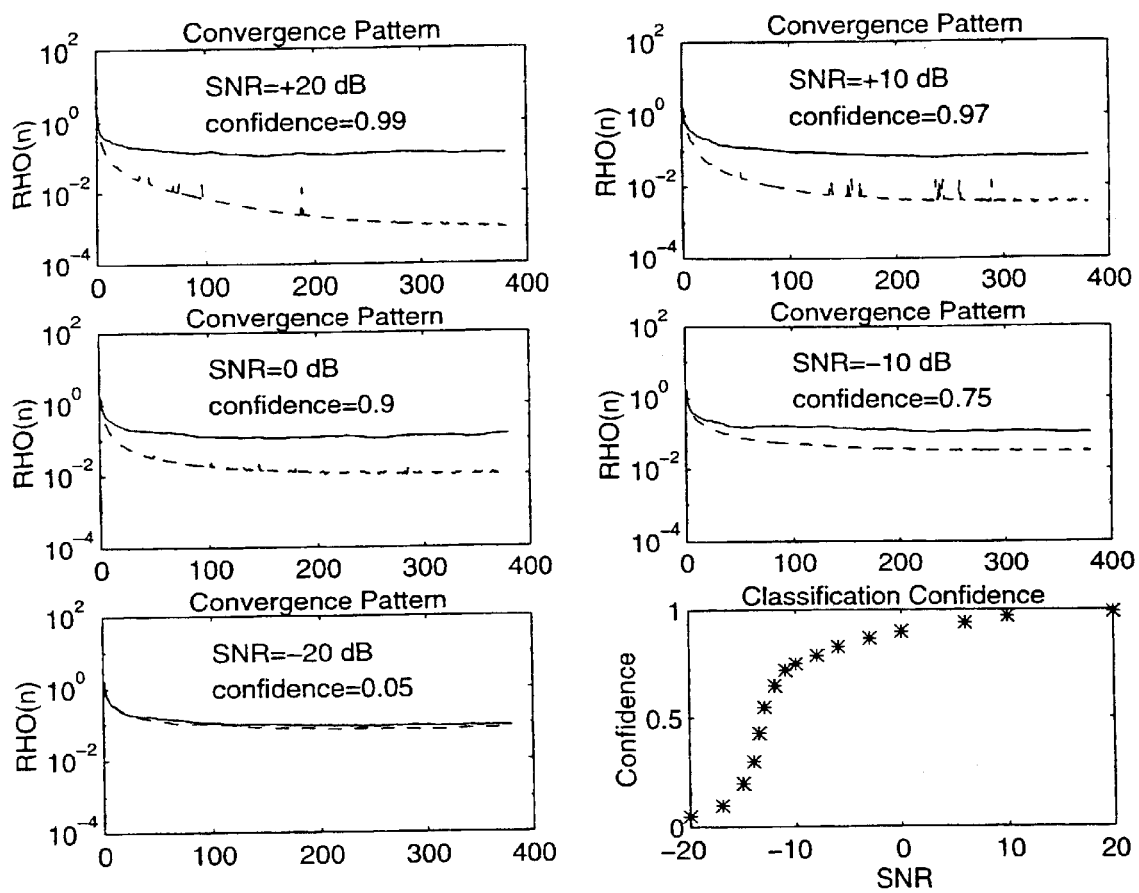
FIG. 7 presents further graphical data regarding the learning process of layer 1.

FIG. 7, which is a dynamic representation of the learning process, shows the convergence patterns and classification confidences of the two neurons, where it can be seen that for SNR's lower than −10 dB the classification confidence declines sharply. The classification results, tested on 100 input vectors, 50 of each category, for each SNR, are presented in the table below; due to the competitive scheme, Positives and False Negatives as well as Negatives and False Positives are complementary.

Identification Performance

Figure 8:
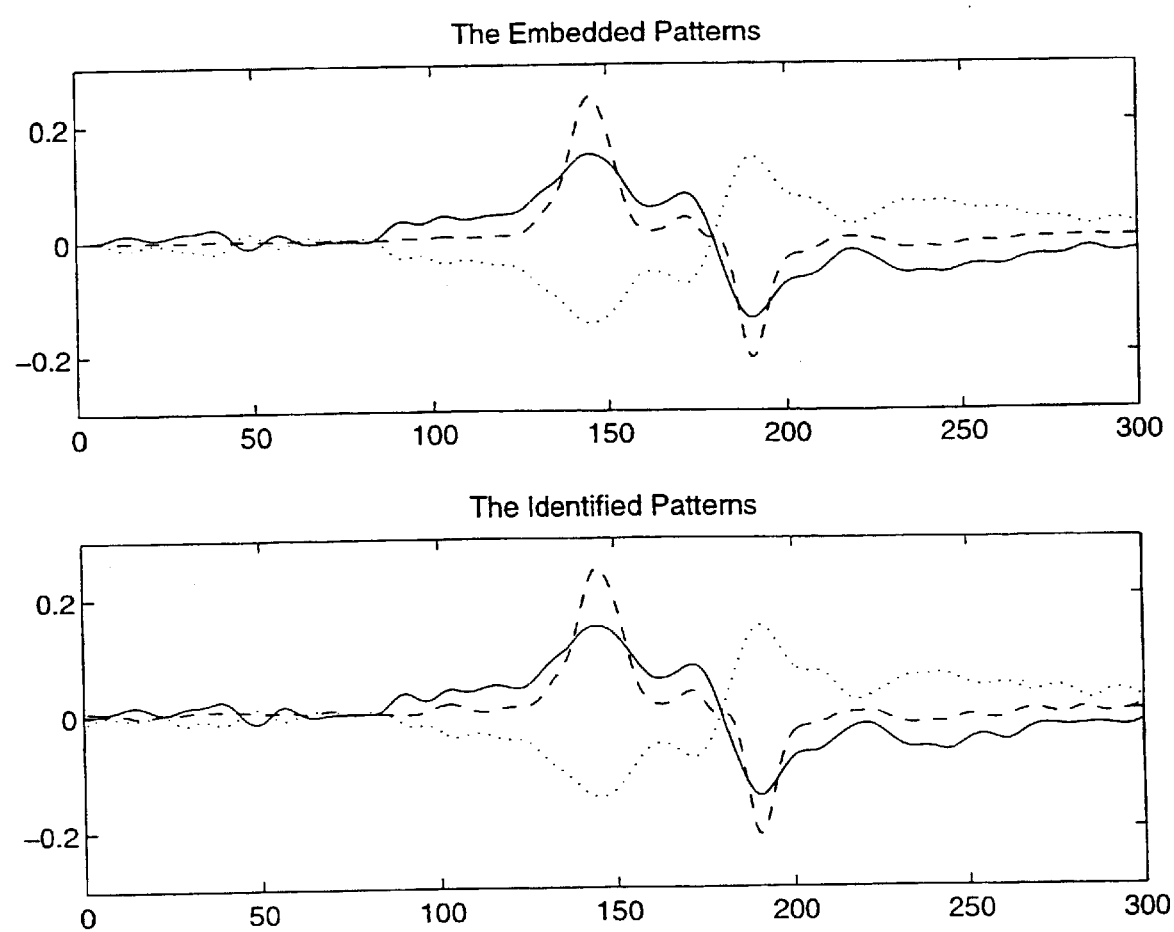
FIG. 8 presents further graphical data regarding the learning process of layer 1.

A second simulation was performed to evaluate the identification capabilities of the network. A typical movement related EP was used to simulate three signal patterns; the EP itself s(n), its cubic representation $s^3(n)$, and its sign inverted version −s(n). The signals were normalized and embedded within simulated EEG at an SNR of −10 dB, in 500 realizations with identical probability of appearance of each pattern. The network was able to identify the embedded patterns with high precision, justifying its use as an identification network. FIG. 8, top, illustrates simulated signal patterns, comprising of an averaged MRP waveform (solid), its sign inverted version (dotted), and its cubic version (dashed); all signals are normalized and embedded within an additive Gaussian noise at an SNR of −10 dB. FIG. 8, bottom, illustrates the patterns identified by the PR layer, which are practically identical to the embedded patterns. The dynamic identification process is demonstrated in the Appendix.

Consistency Verification

Figure 9:
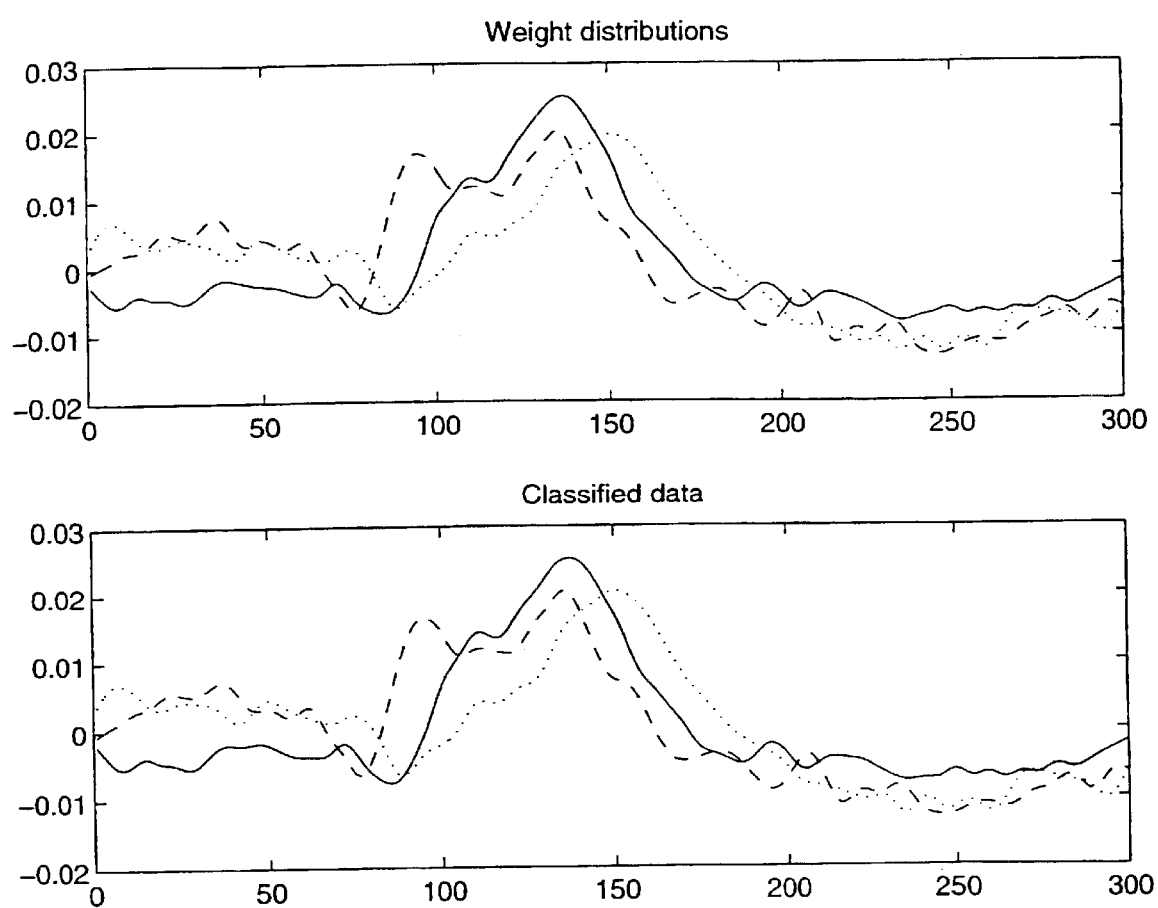
FIG. 9 presents further graphical data regarding the learning process of layer 1.

Finally, consistency of the identified EP's should be demonstrated, in the sense that the identified EP types (represented via the network weights) coincide with the a-posteriori classification obtained with the converged set of correlation filters. To demonstrate the consistency, real EP data whose categorization yielded three signal types are used. The experiment included auditory stimulation at variable intensities, to be described later in the decomposition section. The identification results, compared to the classified patterns, are presented in FIG. 9. The identified EP types and the a-posteriori average of the classified patterns can be seen to practically coincide.

4.5 Experimental Study 4.5.1 Motivation

An important task in ERP research is the identification of effects related to cognitive processes triggered by meaningful versus non-relevant stimuli [e.g. Pratt et. al., 1989]. A common procedure to study these effects is the classic odd-ball paradigm, where the subject is exposed to a random sequence of stimuli and is instructed to respond only to the task-relevant stimuli (referred to also as Target stimuli). Typically, the brain responses are extracted via selective averaging of the recorded data, ensembled according to stimulus context. This method of analysis assumes that the brain responds equally to the members of each type of stimulus; however the validity of this assumption is unknown in the above case where cognition itself is being studied. Using the proposed approach, a-priori grouping of the recorded data is not required, thus overcoming the above severe assumption on cognitive brain function. The experimental paradigm and the identification results of applying the proposed method are described below.

4.5.2 Experimental Paradigm

Cognitive event-related potential data were acquired during an odd-ball type paradigm from electrode Pz referenced to the mid-lower jaw [Jasper, 1958], with a sample frequency of 250 Hz. The subject was exposed to repeated visual stimuli, consisting of the digits '3' and '5', appearing on a PC screen. The subject was instructed to press a push-button upon the appearance of '5'—the Target stimulus, and ignore the appearances of the digit '3' [Lange at. al., 1995].

With odd-ball type paradigms, the Target stimulus is known to elicit a prominent positive component in the ongoing brain activity, related to the identification of a meaningful stimulus. This component has been labeled $P_{300}$, indicating its polarity (positive) and timing of appearance (300 ms after stimulus presentation). The parameters of the $P_{300}$ component (latency and amplitude) are used by neurophysiologists to assess, among other, effects related to the relevance of stimulus and level of attention [e.g. Lange et. al., 1995; Picton & Hillyard, 1988; Schwent & Hillyard, 1975].

4.5.3 Identification Results

Figure 10:
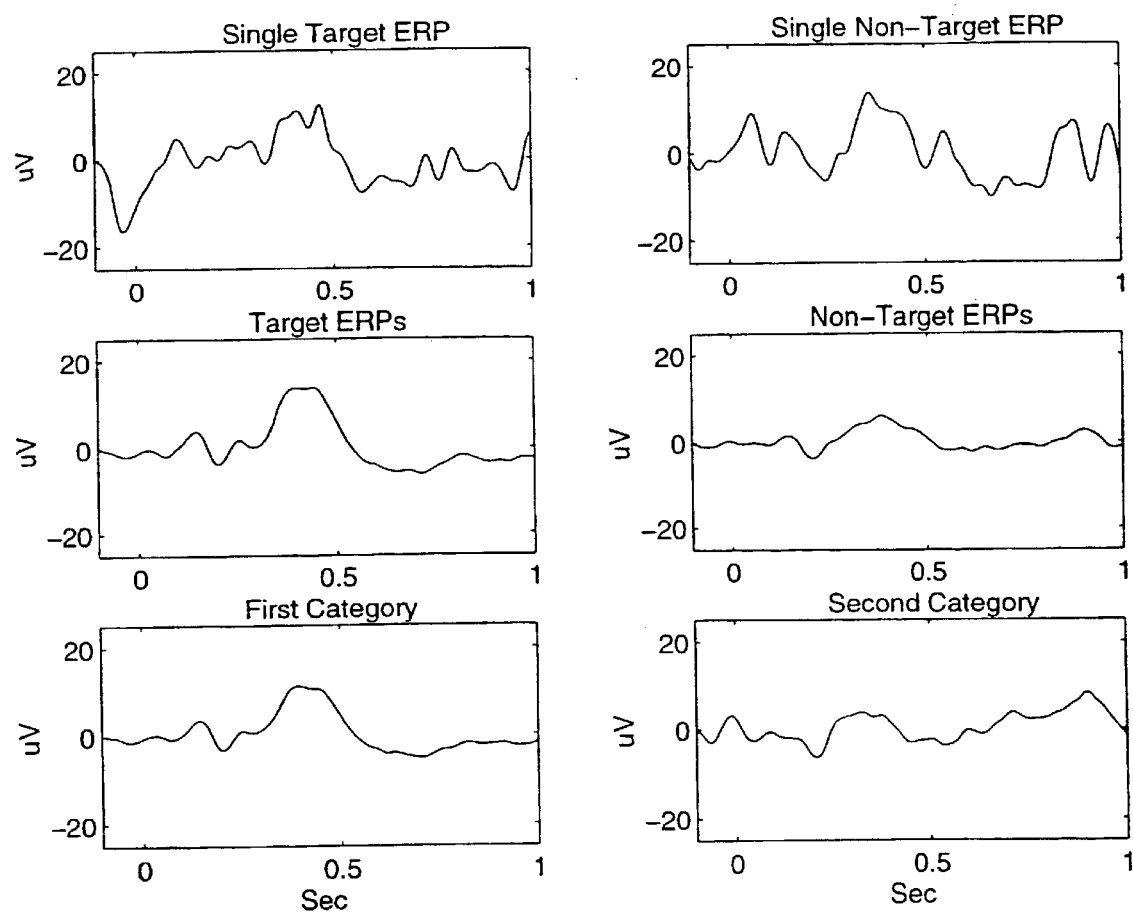
FIG. 10 presents further graphical data regarding the learning process of layer 1.

The competitive ANN was trained with 80 input vectors, half of which were Target ERP's and the other half were Non Target. The network converged after approximately 300 iterations (per neuron), yielding a reasonable confidence coefficient of 0.7. Samples of two single-trial post-stimulus sweeps, of the Target and Non-Target averaged ERP templates, and of the ANN identified signal categories, are presented in FIG. 10. Thus, FIG. 10 illustrates stimulus related selective averaging versus spontaneous categorization: top—sample sweeps, middle—standard templates, bottom—the ANN categorized patterns.

Figure 11:
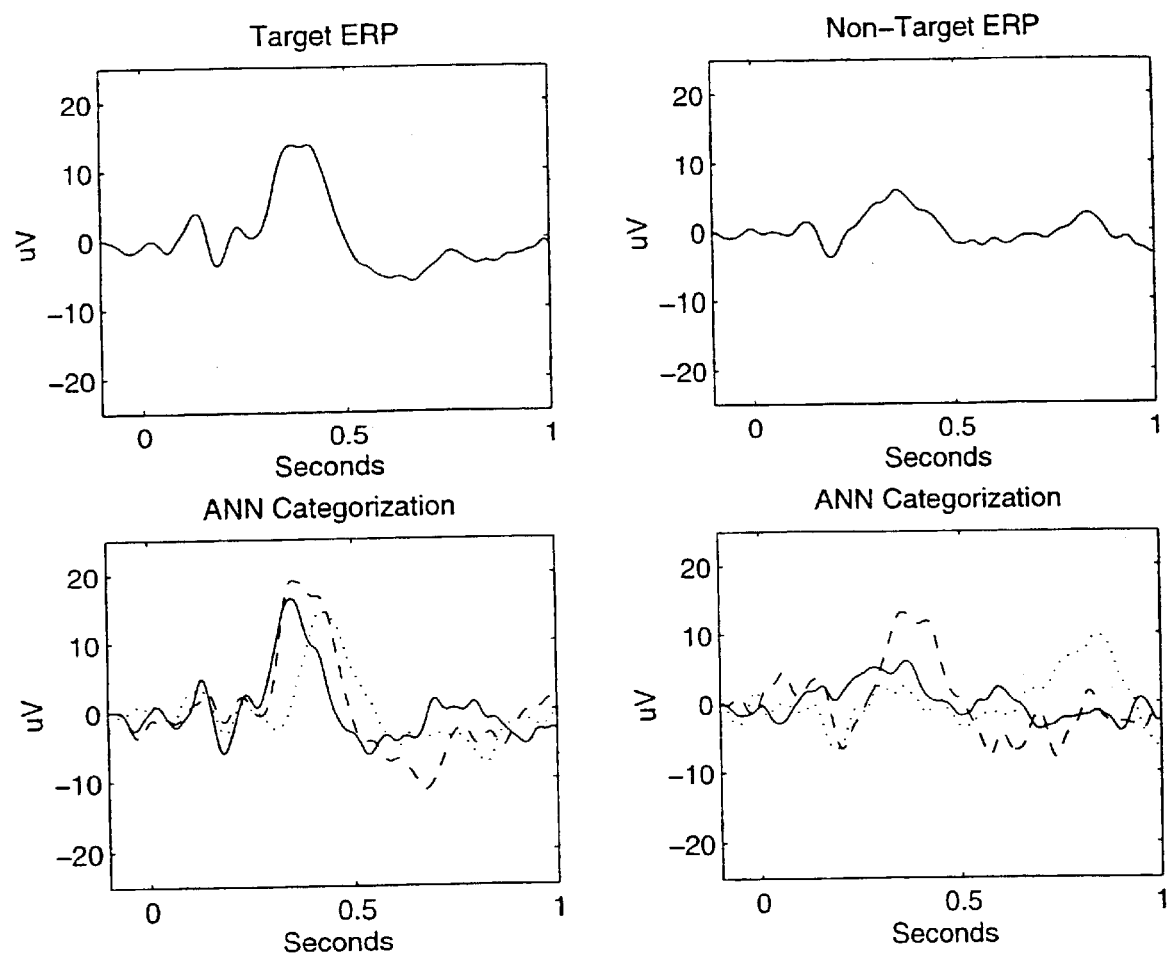
FIG. 11 presents further graphical data regarding the learning process of layer 1.

The automatic identification procedure has provided two signal categories, similar to the stimulus-related selective averaged signals, but requiring further examination due to the slight differences between the selectively averaged waveforms and the categorization obtained by the ANN. The dynamic identification process is shown in the Appendix. The categorization process was consequently repeated, this time using Target and Non-Target data separately; the results are presented in FIG. 11: top—standard averages, bottom—the ANN categorizations. The categorization of Target data yielded 3 ERP patterns, increasing in latency and corresponding to previous findings of increased latency with prolonged reaction times [Lange et. al., 1997]. Non-Target epoch analysis yielded a Target-like $P_{300}$ waveform meaning that, at least occasionally, Target-like $P_{300}$ appears even with Non-Target stimuli. This accounts for the above differences and obviously requires further investigation as to the credibility of selective event related data averaging when applied in the context of analysis of cognitive brain function.

4.6 Discussion

It was shown via simulation as well as via analysis of real EP data that variable signal patterns can be identified and extracted from noisy realizations, relaxing the heavy assumption of pattern invariability and thus overcoming the need for stimulus-related selective averaging.

The simulation study demonstrated powerful capabilities of the competitive ANN in identifying and classifying the low amplitude signals embedded within the large background noise. The detection performance declined rapidly for SNR's lower than −15 dB, which is in general agreement with the theoretical statistical results; loss of significance in detection probability is evident for SNR's lower than −20 dB. Empirically, high classification performance was maintained with SNR's of down to −10 dB, yielding confidences in the order of 0.7 or higher.

The experimental study presented an unsupervised identification and classification of the raw data into Target and Non-Target responses, dismissing the requirement of stimulus- or event-related selective data grouping. The identified patterns generally resemble conventional selective-average analysis, yet the obtained differences have been identified to be the result of unexpected appearance of $P_{300}$-like responses in the Non-Target data, further validating the method and presenting its added value in terms of enhanced insight into brain operation compared to the conventional averaging analysis.

The presented results indicate that the noisy single-trial brain responses may be identified and classified objectively in cases where relevance of the stimuli is unknown or needs to be determined, e.g. in man-machin communication [Farwell & Donchin, 1988] or in lie-detection scenarios [Farwell & Donchin, 1991; Lange & Inbar, 1996c], and thus provide objective insight into brain function.

5 Decomposition of EP Waveforms 5.1 Introduction

Transient evoked brain potentials are elicited in response to various external stimuli, having different time-course with varying characteristics depending on various parameters among which are the nature and complexity of the applied stimulus, its associated task, and the subject's state of mind. It is well established that different components of the evoked potential complex may originate from different functional brain sites, and can sometimes be distinguished by their respective latencies and amplitudes [Donchin, 1966].

An important issue in evoked potential research is assessment of the extent to which an EP complex varies with the manipulation of experimental parameters, in an attempt to utilize the identified variations as insight into brain and central nervous system function. Physiological interpretations are often given to local variations of EP peaks by analyzing the entire signal complex, while ignoring cross-peak effects caused by the close proximity of the peaks, where a slight change of amplitude or latency of a single component may significantly alter the appearance of adjacent component peaks.

The issue of EP decomposition is thus of major significance as component analysis is at the core of EP variability analysis. Changes in component parameters (latency and amplitude) can have profound interpretations in EP based diagnostical evaluations. Decomposition methods vary from simple peak analysis methods, through analytical modeling attempts to approximate EP components, and to purely mathematical methods which do not consider the physiological origin of the signals at hand [Roterdam, 1970].

Evoked Potentials have been decomposed via three common methods: (1) Peak Analysis, treating peaks of the EP complex as independent components, (2) Inverse Filtering, where the EP complex is filtered to extract the component parameters, and (3) Principal Component Analysis, which is equivalent to Karhunen-Loeve' decomposition of the data ensemble.

In this chapter, a statistical method for robust decomposition of an EP complex into a set of distinctive components is presented [Lange & Inbar, 1986b]. The model assumes linear superposition of the EP constituent components, and Gaussian distributed firing instants of the neuronal population associated with each component. The decomposition provides a loss-less description of the EP complex, which is demonstrated via computer simulations as robust to violations of the model assumptions. The decomposition method is applied to experimental data, demonstrating its separation performance of severely overlapping EP components.

5.2 Model and Assumptions

Donchin's definition of evoked potential components, suggesting that an evoked potential complex represents a sequence of events, triggered successively in different cortical structures by the stimulus, is adopted in this work. The contribution of one such event to the EP complex will be considered as an EP component. In addition, it is assumed that the EP waveform is formed by a superposition of the components, where trial to trial variability may be accounted for by adapting the respective amplitudes and latencies of the individual components. In devising an appropriate decomposition rule, the following two points were considered:

- The decomposed waveforms should look 'natural', that is they should not appear as synthetic to the neurphysiologist. This implied using a loss-less procedure to ensure that fine detail, perhaps insignificant in terms of MSE but with potentially substantial diagnostic value, would not be lost.
- Dealing with an inverse problem task, of inherently infinite solutions, the method should be of a data-driven type rather than a mathematically constrained solution. This has led to using a statistical modeling approach of mass neural activity, as described in the following.

5.3 Decomposition Rule

The EP component generation mechanisms consist of vast neural populations which fire synchronously. It is therefore only logical to use a decomposition method based on the nature of neuronal activity. In the general case, if neural activity has to pass through N synaptic stations each producing a delay of D with a variance $\sigma^2$, the total delay would be [Abeles et. al., 1993]:

$$\text{DELAY} = N \cdot D \pm \sigma \cdot \sqrt{N} \qquad (25)$$

Thus the firing instants of a mass population of synchronized neurons may be assumed to be governed by Gaussian probability distributions. Moreover, due to the relatively short duration of the Action Potential (few msec) compared to the EP component duration (hundred msec), the probability distributions of the component neuronal sources may be approximated from the components of the measured signal complex, assuming Gaussian firing patterns of the involved neural populations. An initial approximation of the mean value is extracted from the points of maximum activity (peak amplitude), and the approximate variance is implied by peak width.

The initial approximation serves as a starting point for a standard gradient search of the optimal parameters.

The EP waveform is assumed to consist of a superposition of P components:

$$s(t) = \sum_{i=1}^{P} k_2 \cdot v_2(t - \tau_2) \qquad (26)$$

$v_i(t)$ represents the basic shape of the i-th component, $\tau_i$ indicates the component latency, and $k_i$ refers to the component amplitude. Let us denote with $A_t$ the set of firing neurons $\{a_t\}$ at time instant t, with $A_t^j$ being a subset of $A_t$, $A_t^j \subset A_t$, which represents the neural batch responsible for the j-th component, where $\cup A_t^j = A_t$ and $\cup A_t^j = \phi$. Let $\{d_i, i=1, 2, \ldots, P\}$ denote the set of probability distributions of neuronal firing instants for the p components.

The decomposition is calculated by dividing each data point among the component sources according to their relative contributions, which can be estimated as the probability of a neuron from batch j to fire at instant t normalized by the sum of probabilities of neurons from all neural batches to fire at time instant t:

$$v_j(t) = s(t) \cdot \frac{Pr\{a_t^j\}}{\sum_{i=1}^{p} Pr\{a_t^2\}} \qquad (27)$$

$$= s(t) \cdot \frac{\lim_{\Delta \to 0} \int_{t-\Delta}^{t+\Delta} d_j(s) ds}{\sum_i \lim_{\Delta \to 0} \int_{t-\Delta}^{t+\Delta} d_i(s) ds} \qquad (28)$$

$$= s(t) \cdot \frac{2\Delta \cdot d_j(t)}{\sum_2 2\Delta \cdot d_i(t)} \qquad (29)$$

yielding (30)

$$v_j(t) = s(t) \cdot \frac{d_j(t)}{\sum_{i=1}^{p} d_2(t)}; j = 1, 2, \ldots, P.$$

Applying the assumption of Gaussian distributed firing instants, yields the decomposition rule:

$$v_j(t) = s(t) \cdot \frac{\sigma_j^{-1} \exp\left(-\frac{(t-\tau_3)^2}{2\sigma_j^2}\right)}{\sum_{i=1}^{p} \left[\sigma_i^{-1} \exp\left(-\frac{(t-\tau_i)^2}{2\sigma_i^2}\right)\right]} \qquad (31)$$

As noted above, initial estimates of $\tau_i$ and $\sigma_i$ are extracted from peak attributes of the signal complex and are used as a starting point for a gradient search algorithm based on a least squares fitting criterion. It is worth mentioning here that the assumed Gaussian distributions used for the decomposition process are not imposed on the resulting decomposed waveforms, which is the case with some other methods [e.g. Geva et. al., 1996]. The decomposition would perfectly describe the underlying components if the assumed distributions are correct, nevertheless moderate deviations would not significantly distort peak amplitudes and latencies but might affect the overlapping component tails; this is not crucial, however, since neurophysiologists are mostly concerned with peak parameters (latency and amplitude), rather than with waveform morphology. It should also be noted that, if appropriate, the Gaussian distribution law can be modified and easily substituted in Eq. 33.

Figure 12:
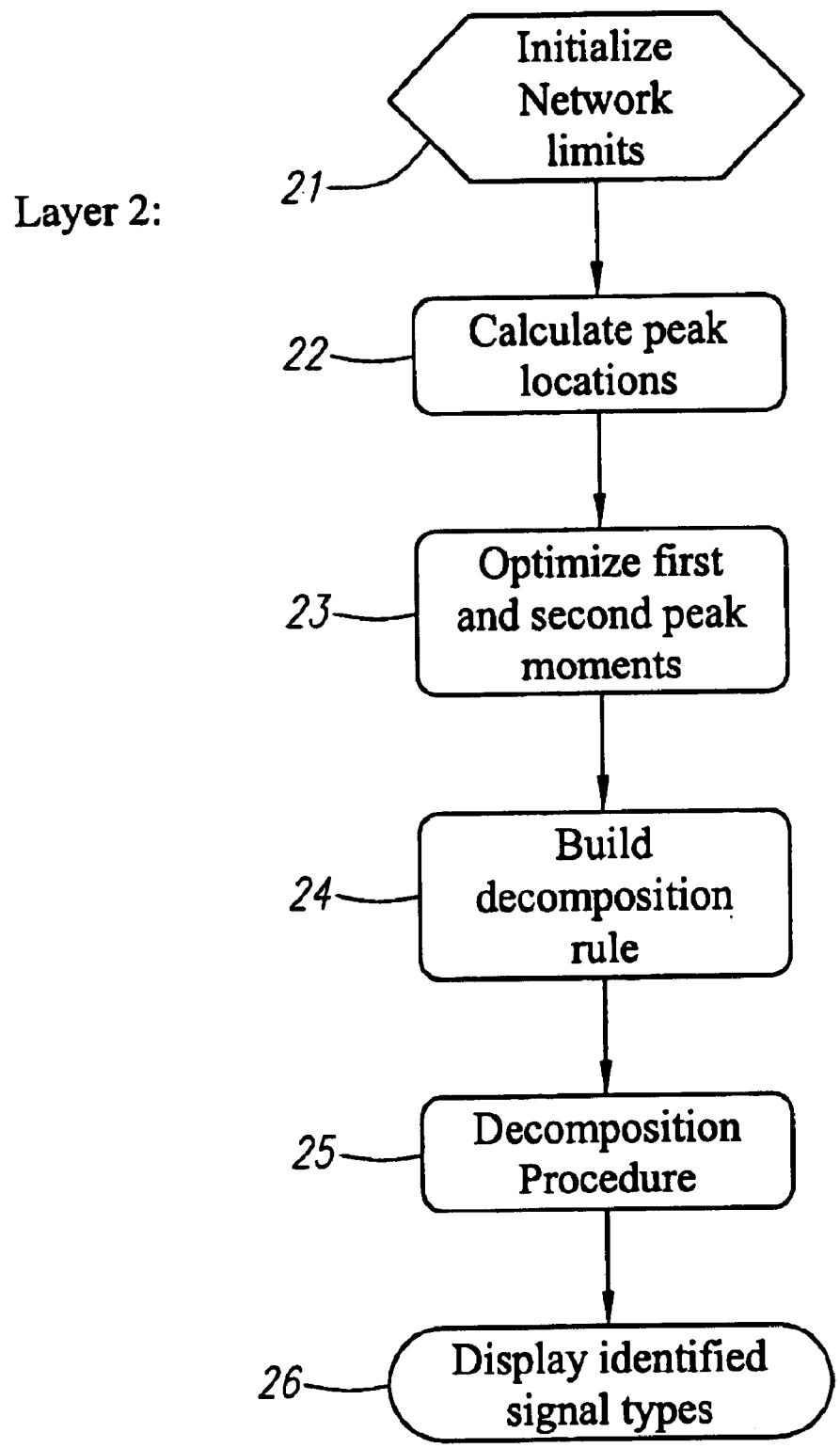
FIG. 12 is a flow chart illustrating the decomposition process performed by layer 2.

The foregoing decomposition process performed by layer 2 in FIGS. 2 and 3 is illustrated by blocks 21–26 in the flow chart of FIG. 12.

5.4 Simulation Results

Figure 13:
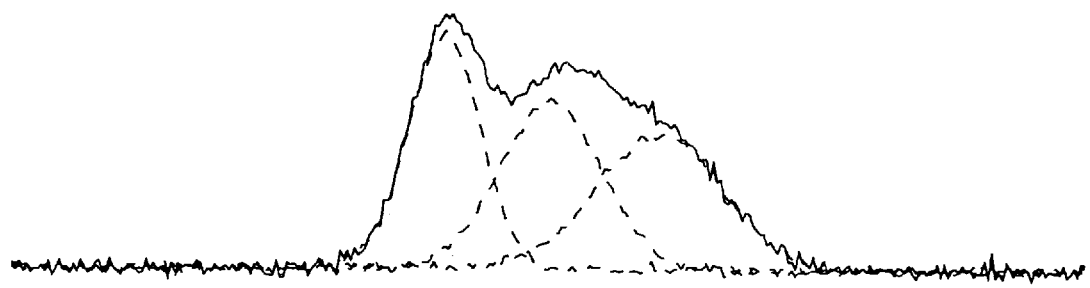
FIG. 13 presents graphical data regarding the decomposition process performed by layer 2.
Figure 13:
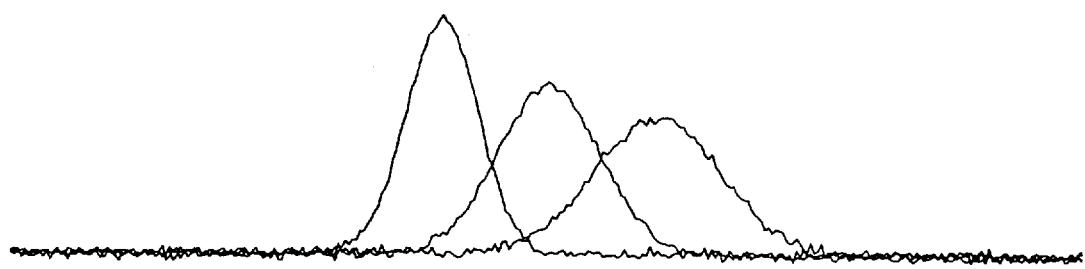

Computer simulations were conducted to assess and verify the performance of the proposed decomposition scheme, with special emphasis on its robustness to violation of the assumptions. The purpose of the first simulation is to demonstrate the decomposition performance without violation of the assumptions, i.e. when the firing instants of the component sources adhere to Gaussian laws. Three sources are simulated, each consisting of 10,000 firing neurons, with a major temporal overlap of the middle and right-hand components. FIG. 13 shows the synthesized signal complex and its decomposition, where the resulting components practically coincide with the embedded components.

Figure 14:
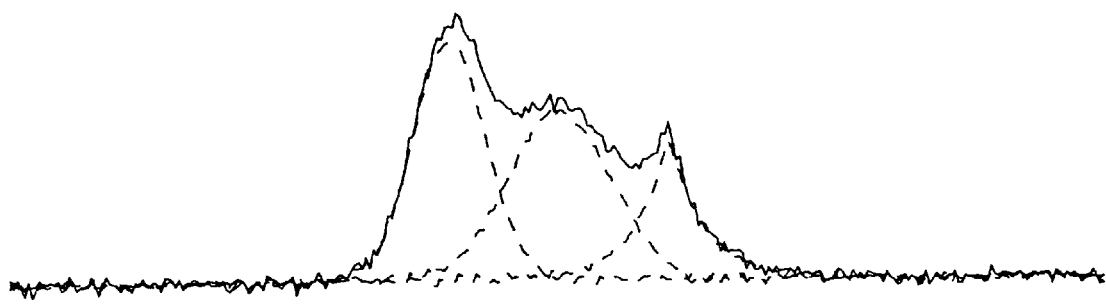
FIG. 14 presents further graphical data regarding the decomposition process performed by layer 2.
Figure 14:
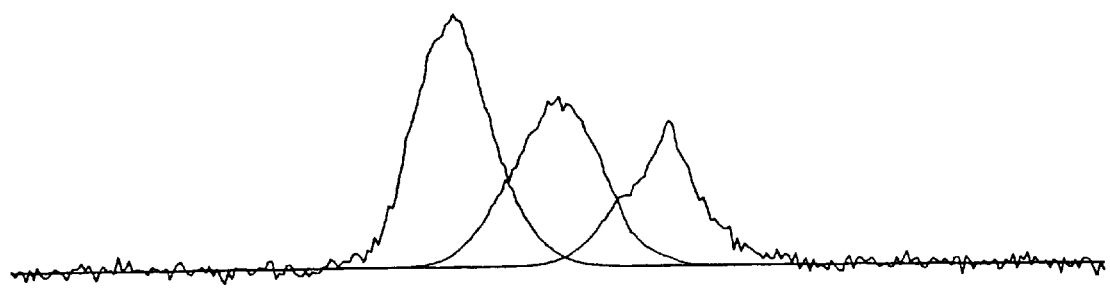

The second simulation demonstrates the performance under a major violation of the assumptions. The right-hand component is modeled with a two-sided exponentially distributed source, while the other component sources remain intact. FIG. 14 illustrates the simulation results: top—a synthesized EP and its underlying components, bottom—decomposition results. It can be seen that the decomposition retains its high quality in spite of the major violation of the distribution of the right-hand component, yielding only a relatively small error, mainly in the overlapping tails of the middle and right-hand components.

5.5 Experimental Results

Figure 15:
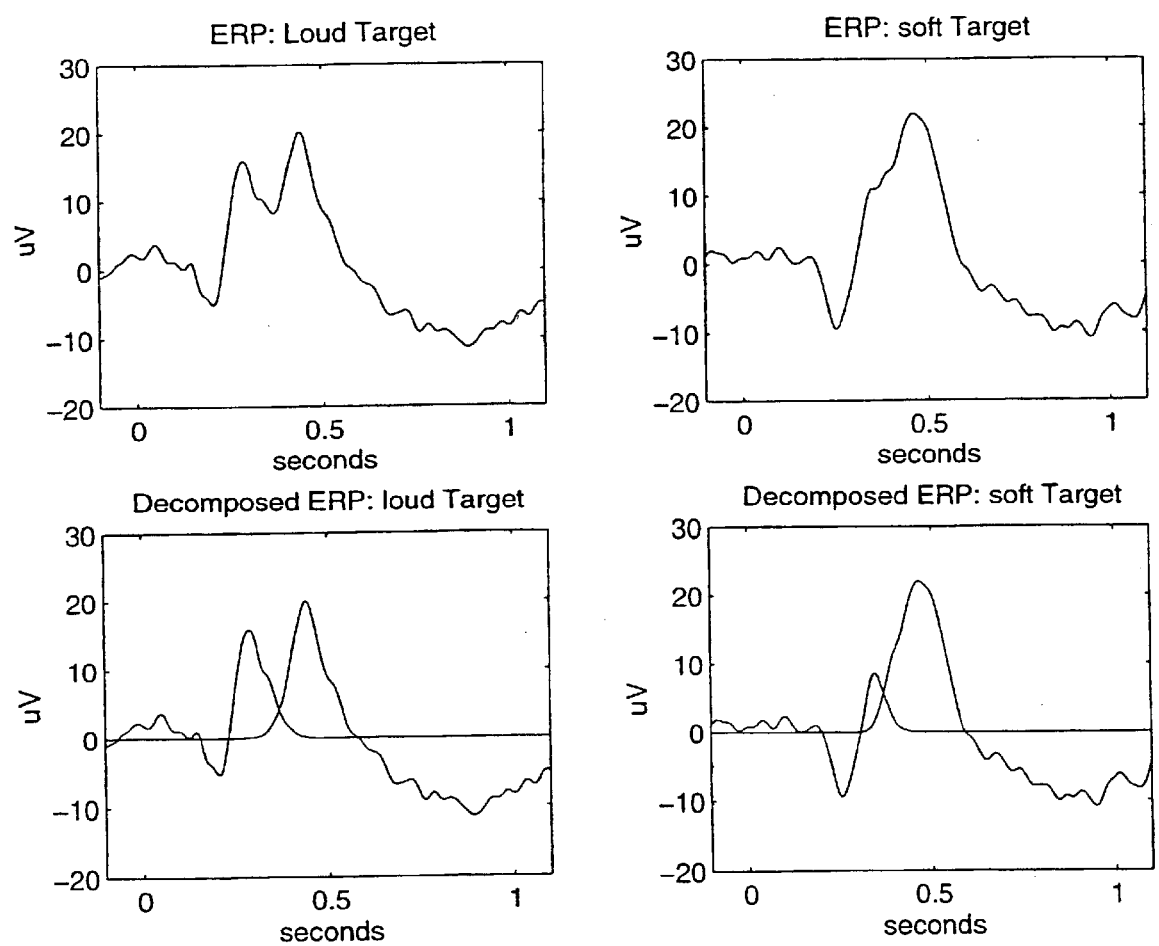
FIG. 15 presents further graphical data regarding the decomposition process performed by layer 2.

Event Related Potential data which include a substantial temporal overlap of a stimulus-related (P2) component and a cognitive (P3) component are investigated, where the degree of temporal overlap depends on the physical magnitude of the stimulus. The experiment included an odd-ball type task, where upon recognition of an auditory rare stimulus the subject was instructed to hit a push-button. The paradigm was performed in two sessions, with a 20 dB power decrease of the target stimulus in the second session. FIG. 15 shows the EP's associated with the loud and soft targets, and their respective decompositions. The temporal overlap of P2 and P3 is increased with low stimulus intensities. Obviously, the resulting components to not appear Gaussian. Yet near-peak characteristics can be approximated with a Gaussian waveform, justifying the decomposition technique; alternatively, the left components of the soft target stimulus could be modeled as a sum of two Gaussian waves and decomposed accordingly. The results present means for quantitative analysis of the overlapping signals, which could not be performed with the raw averaged waveform.

5.6 Discussion

A statistical method for EP template decomposition was proposed. The method is a compromise between the oversimplistic peak analysis on one hand, and purely mathematical approaches on the other hand. The former suffers from cross peak effects due to componental overlap, biasing the analysis, while the latter relies on mathematical principles like componental orthogonality which are generally not justifiable with biological signals.

The decomposition method proposed herein enables lossless decomposition of the evoked potential complex into constituent components. The data-driven method has been shown as robust to violation of the assumed component distributions, providing high quality decompositions with highly overlapping constituents both in simulations and with real evoked potential data.

Not only informative by themselves, the decomposed constituents are used as input to the following third and final processing layer, which is responsible for the identification of latency and amplitude variations of the EP components embedded within each single-trial recording, as described in the next chapter.

6 Modeling of the Signal Generation Mechanism

6.1 Introduction

Using the pattern identification and statistical decomposition units described in the previous chapters as preprocessing stages, a comprehensive parametric signal generation model is constructed. The EEG is modeled via autoregressive (AR) analysis and the EP is modeled as a sum of FIR filtered EP components [Box & Jenkins, 1976; Makhoul, 1975]. The model is designed to account for small latency and amplitude variations of the signal components from trial to trial, assuming that large variations will have been taken care of by the pattern identification structure described earlier. A block diagram of the parametric signal generation mechanism is presented in FIG. 16. The model assumptions are as follows:

1. The EP and EEG are additively superpositioned in each recorded sweep.
2. The signal and noise in each sweep are uncorrelated.
3. The post-stimulus EEG in each sweep can be adequately modeled with a pre-stimulus adapted AR model.
4. The single-trial EP can be modeled as a superposition of latency and amplitude corrected components of a specific library waveform.

The first two assumptions are, again, conventional assumptions used throughout this work. The third assumption is borrowed from the field of EEG analysis, where it has gained popularity almost as equal to averaging in EP analysis. The fourth assumption reflects the essence of variability analysis capabilities of the proposed model.

As aforementioned, this last processing layer is the most restricting one, its validity resulting from the flexibility and robustness of the previous layers; the first layer identifies a family of responses creating the library of EP template responses, the second layer decomposes the obtained library items, and thus the third layer can rely on the above fourth assumption with much confidence.

6.2 The Parametric Model

Figure 16:
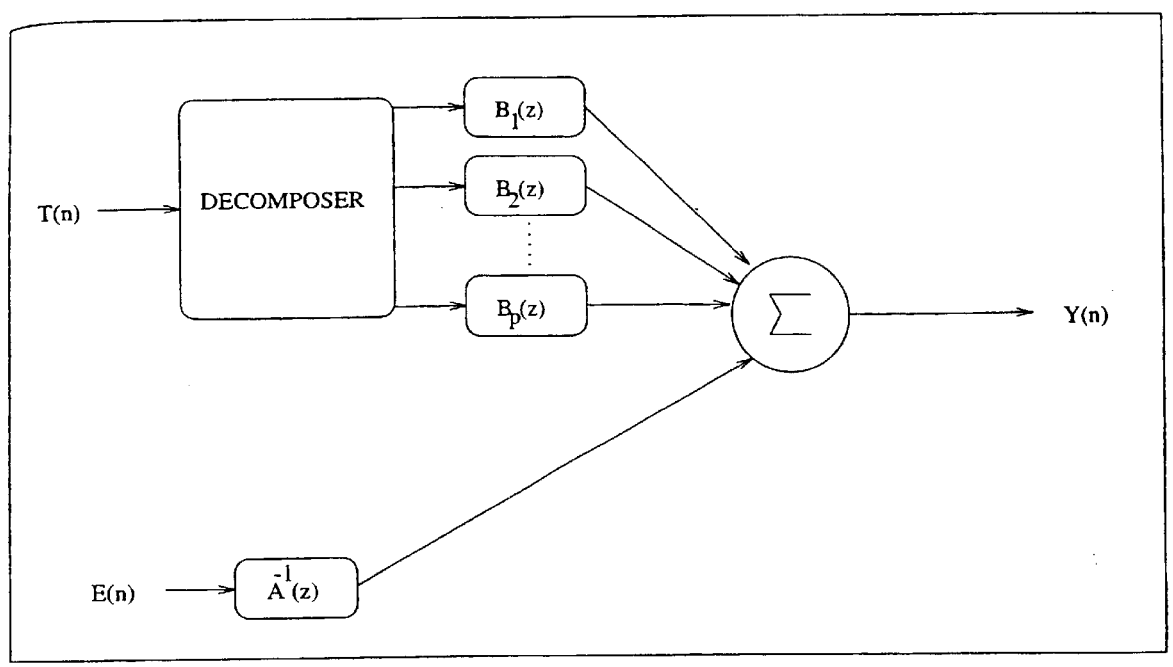
FIG. 16 presents a block diagram and flow chart illustrating the signal synthesis model involved in the process performed by layer 3 of FIG. 1.

FIG. 16 is a block diagram of the signal synthesis model. T,E and Y represent the library matching item (template), a white Gaussian noise series and the recorded single sweep, respectively. $B_i(z)$ are the component latency and magnitude correcting filters. Once optimized, the model provides the two assumed signal contributions, namely the ongoing brain activity and the single-trial evoked brain response.

The notations used throughout the formulations are those of FIG. 16. The model equation in the Z-transform domain is given by:

$$Y(z) = \sum_{i=1}^{p} B_i(z) \cdot T_i(z) + \frac{1}{A(z)} \cdot E(z), \tag{32}$$

where $Y(z)$, $T(z)$ and $E(z)$ represent the measured process, a library EP template and a Gaussian white noise series, respectively. Assuming stationarity of the background EEG, which is verified in the experimental analysis section, $A(z)$ may be identified from pre-stimulus data via autoregressive modeling, and used for post-stimulus analysis. The template and measured EEG are filtered through the identified $A(z)$ to whiten the background EEG signal and thus facilitate closed form least square solution of the model; having to estimate only $B_i(z)$ from the post-stimulus data simplifies the solution process, avoiding the need for iterative identification of the model parameters. The model can be described with the following regression type formula, where the apostrophe denotes whitened signals:

$$y'(n) = \sum_{i=1}^{p} \sum_{j=-d}^{d} b_{i,j} \cdot T'_i(n-j) + e(n) \tag{33}$$

Matrix notation is used to solve the model. Let $y'^T$ be the whitened measurements vector, let $A^T$ be the input matrix, and let $b^T$ be the filter coefficients vector, as d defined below:

$$y'^T = [y'(d+1), y'(d+2), \ldots, y'(N-d)] \tag{34}$$

$$A^T = \begin{pmatrix} T'_1(2d+1) & T'_1(2d+2) & \cdots & T'_1(N) \\ T'_1(2d) & T'_1(2d+1) & \cdots & T'_1(N-1) \\ \vdots & \vdots & & \vdots \\ T'_1(1) & T'_1(2) & \cdots & T'_1(N-2d) \\ T'_2(2d+1) & T'_2(2d+2) & \cdots & T'_2(N) \\ \vdots & \vdots & & \vdots \\ T'_2(1) & T'_2(2) & \cdots & T'_2(N-2d) \\ \vdots & \vdots & & \vdots \\ T'_p(2d+1) & T'_p(2d+2) & \cdots & T'_p(N) \\ \vdots & \vdots & & \vdots \\ T'_p(1) & T'_p(2) & \cdots & T'_p(N-2d) \end{pmatrix} \tag{35}$$

$$b^T = [b_{1,-d}, b_{1,-d+1}, \ldots, b_{1,d}, b_{2,-d}, \ldots, b_{p,d}] \tag{36}$$

Using the defined notations, the model can be expressed as follows:

$$y' = A \cdot b + \epsilon, \tag{37}$$

where $\epsilon$ is the vector of prediction errors:

$$\epsilon^T = [e(2d+1), e(2d+2), \ldots, e(N)]. \tag{38}$$

The optimal vector of parameters in the least square sense is:

$$\hat{b} = (A^T \cdot A)^{-1} \cdot A^T \cdot y' \tag{39}$$

6.3 Statistical Evaluation

It can be shown that if the whitened EEG signal is zero mean, then the obtained least square estimator is unbiased, and that for the scalar case (which corresponds to the constant latency case), the estimation variance is proportional to the EEG variance and inversely proportional to the energy of the template.

6.3.1 Estimation Bias

Provided that the vector of prediction errors is zero mean, the least-square solution is unbiased. Assigning the model equation $y' = Ab_0 + \epsilon_0$ to the solution yields:

$$\hat{b} = (A^T A)^{-1} A^T A b_0 + (A^T A)^{-1} A^T \epsilon_0 \tag{40}$$

$$= b_0 + (A^T A)^{-1} A^T \epsilon_0$$

Noting that the product $(A^T A)^{-1} A^T$ is deterministic, we obtain an unbiased estimator:

$$E[\hat{b}] = E[b_0] + (A^T A)^{-1} A^T \cdot E[\epsilon_0] \tag{41}$$

$$= E[b_0]$$

$$= b_0$$

6.3.2 Estimation Variance

Assuming that the vector of prediction errors is a Gaussian white noise process, we can calculate the covariance matrix of the parameter vector $\hat{b}$ as follows:

$$C_{bb} = E\left[(\hat{b} - b_0)(\hat{b} - b_0)^T\right] \tag{42}$$

$$= E\left[(A^T A)^{-1} A^T \epsilon_0 \epsilon_0^T A (A^T A)^{-1}\right]$$

$$= (A^T A)^{-1} A^T \cdot E[\epsilon_0 \epsilon_0^T] A (A^T A)^{-1}$$

Assuming white Gaussian noise ($E[\epsilon_0 \cdot \epsilon_0^T] = \sigma^2 \cdot I$), we derive the estimation variance:

$$C_{bb} = \sigma^2 (A^T A)^{-1} (A^T A)(A^T A)^{-1} \tag{43}$$

$$= \sigma^2 (A^T A)^{-1}$$

It can also be shown that for a Gaussian white innovation process, least square estimation is the best unbiased linear estimation, fulfilling the Cramer-Rao bound for unbiased estimators [Haykin, 1986]. For the scalar case, the latter result reduces to:

$$E\left[(\hat{b} - b_0)^2\right] = \sigma^2 \cdot \left\{\sum_n T^2(n)\right\}^{-1}, \tag{44}$$

which shows that the estimation variance is proportional to the EEG variance and inversely proportional to the energy of the template. The credibility of the estimate should be assessed by verifying that the obtained estimation variances are significantly smaller than the identified parameters.

Figure 17:
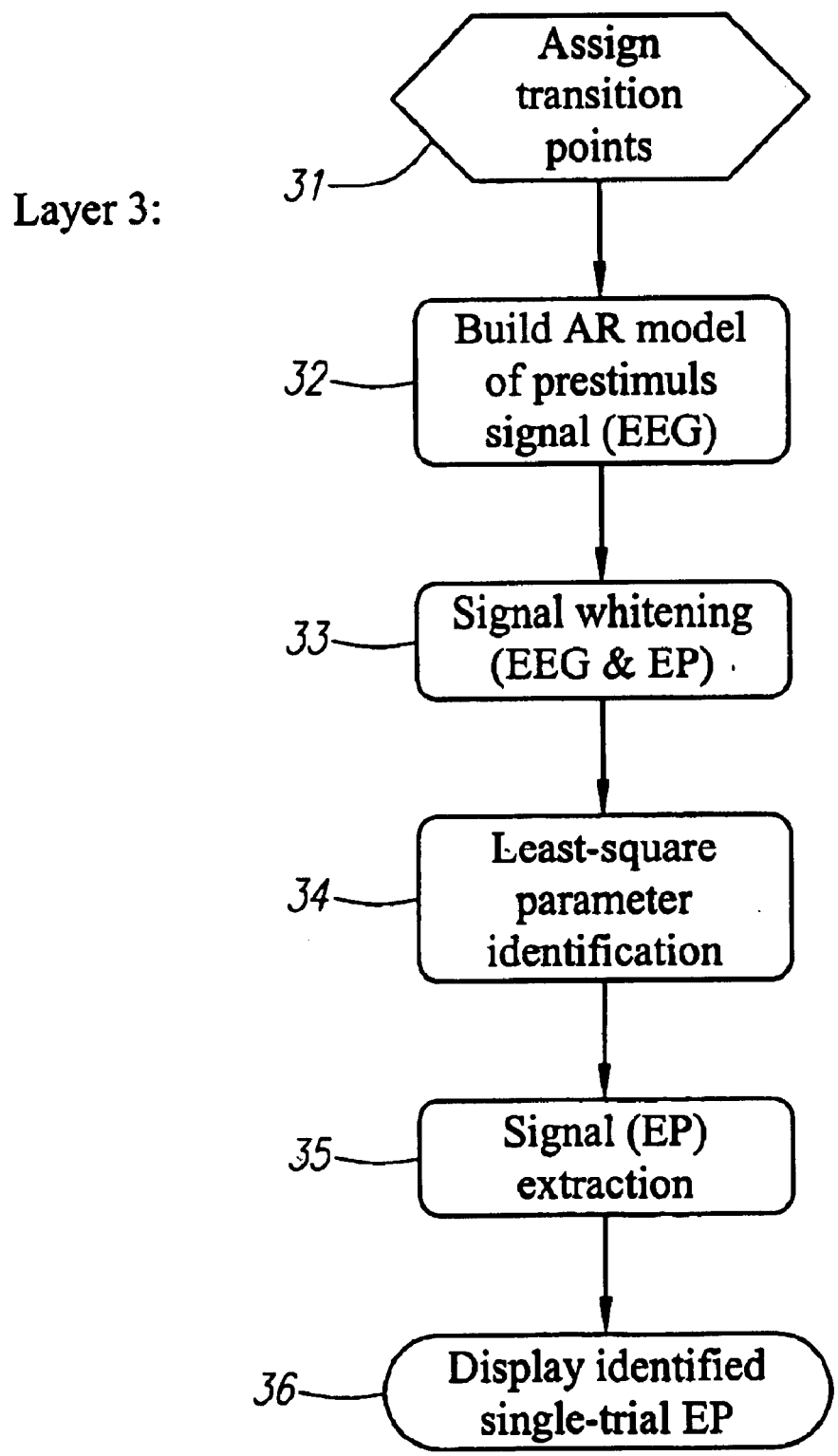
FIG. 17 presents a further block diagram and flow chart illustrating the signal synthesis model involved in the process performed by layer 3 of FIG. 1.

The foregoing steps performed by layer 3 in FIGS. 2 and 3 are indicated by blocks 31–36 in the flow chart of FIG. 17.

6.4 Simulation Study

Figure 18:
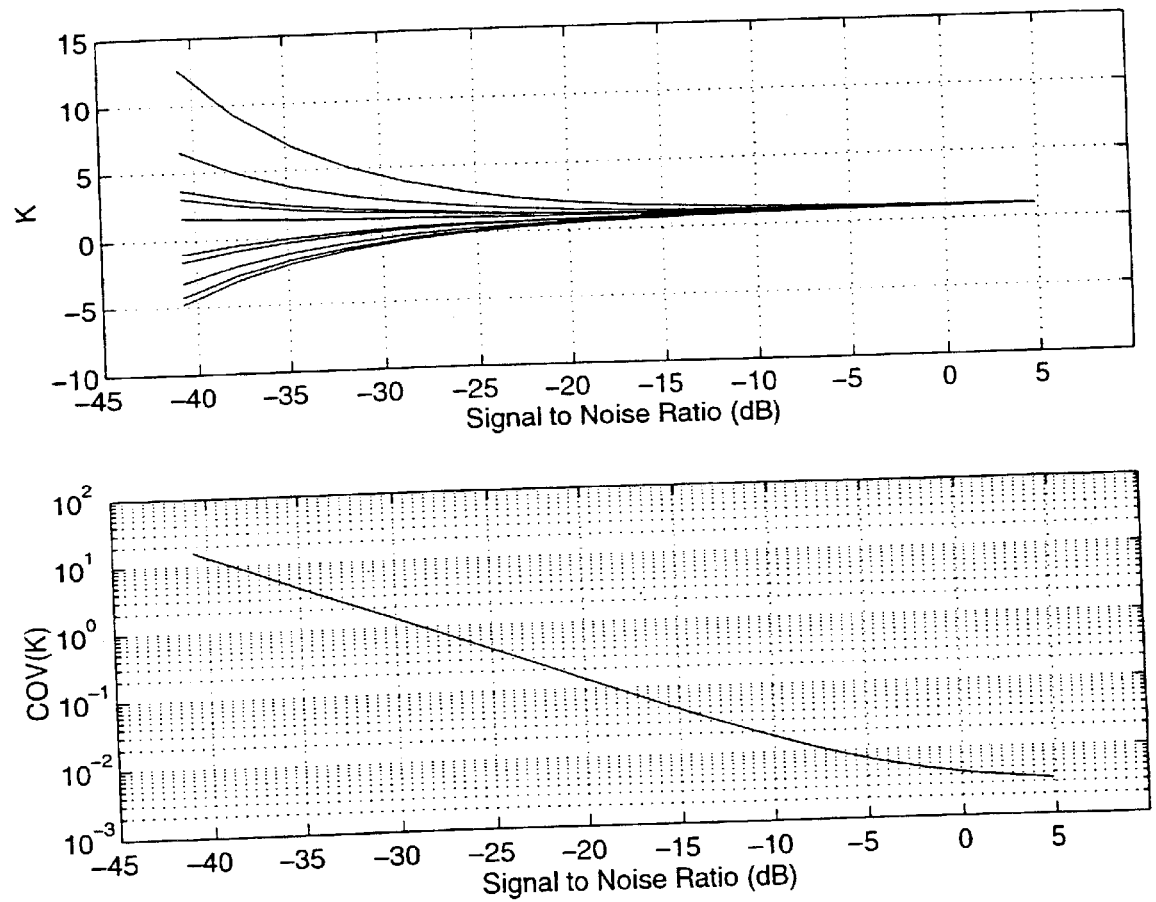
FIGS. 18–25 present graphical data regarding the process performed by layer 3.

First, we study the estimator's performance at varying signal to noise ratios, where the buried response is identical to the template; thus we expect the estimator to yield a scale factor $K \approx 1$, with increasing variances as the SNR decreases. FIG. 18 illustrates an estimation of the gain factor (K) and the variance of estimation as a function of the SNR: top—estimates of K under varying SNR conditions, bottom—theoretical estimation variances. From the estimation results and variances of estimation shown in FIG. 18 it can be seen that the estimation variance is acceptable for SNR's higher than −15 dB, at which point the variance reaches 5%. Consequently, it is necessary to evaluate the SNR of the specific EP's to be analyzed prior to using the suggested estimation algorithm. One possible way to estimate the SNR would be to use the template as a model for the single response and the single epoch recording minus the template as an estimate for the ongoing EEG signal; the error should be small due to the substantially lower power of the embedded response with respect to the ongoing brain activity. Alternatively, the SNR can be approximated from the first layer's confidence coefficient (see Eqs. 24 & 27). The effect of decomposition on these results may be evaluated using Eq. 52, which presents an inversely proportional relation between the signal's energy and variance of estimation.

Figure 19:
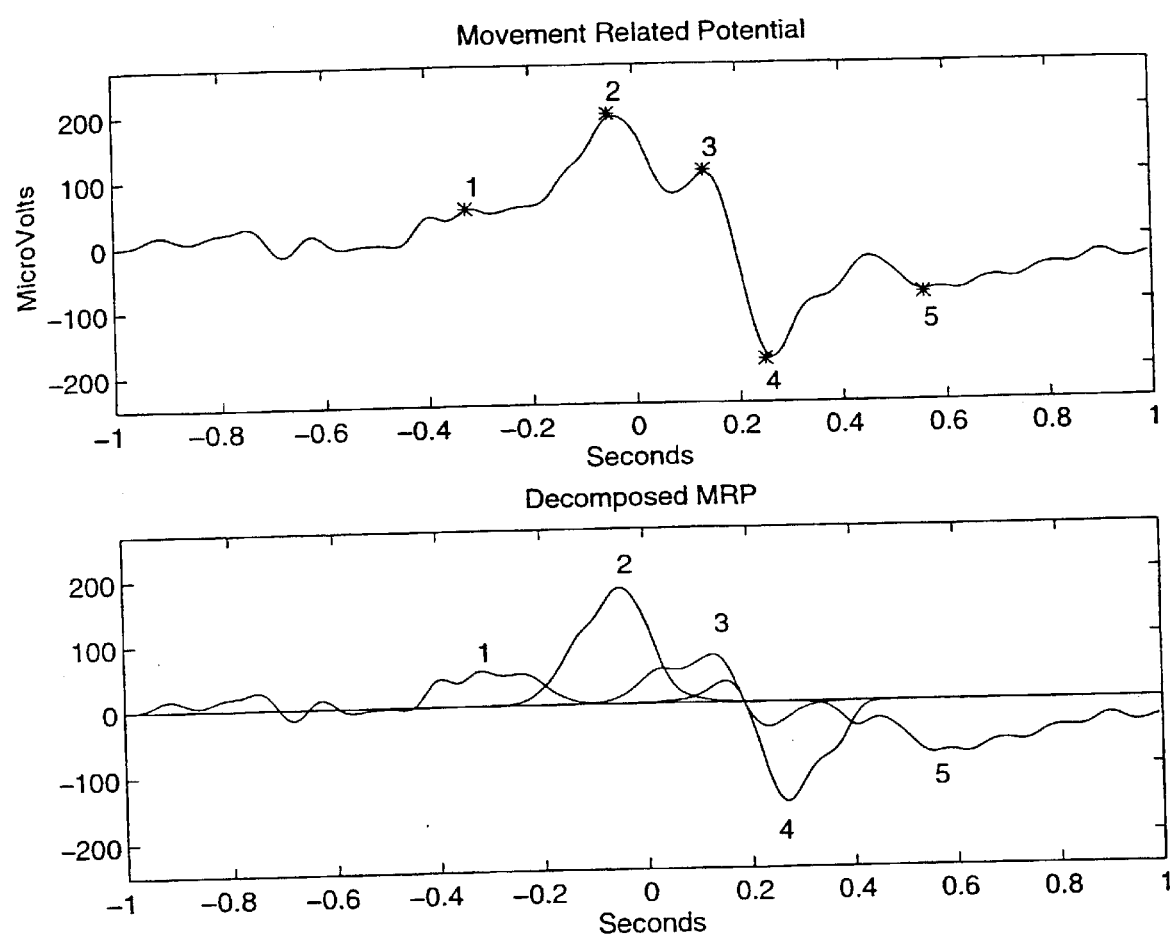
Figure 20:
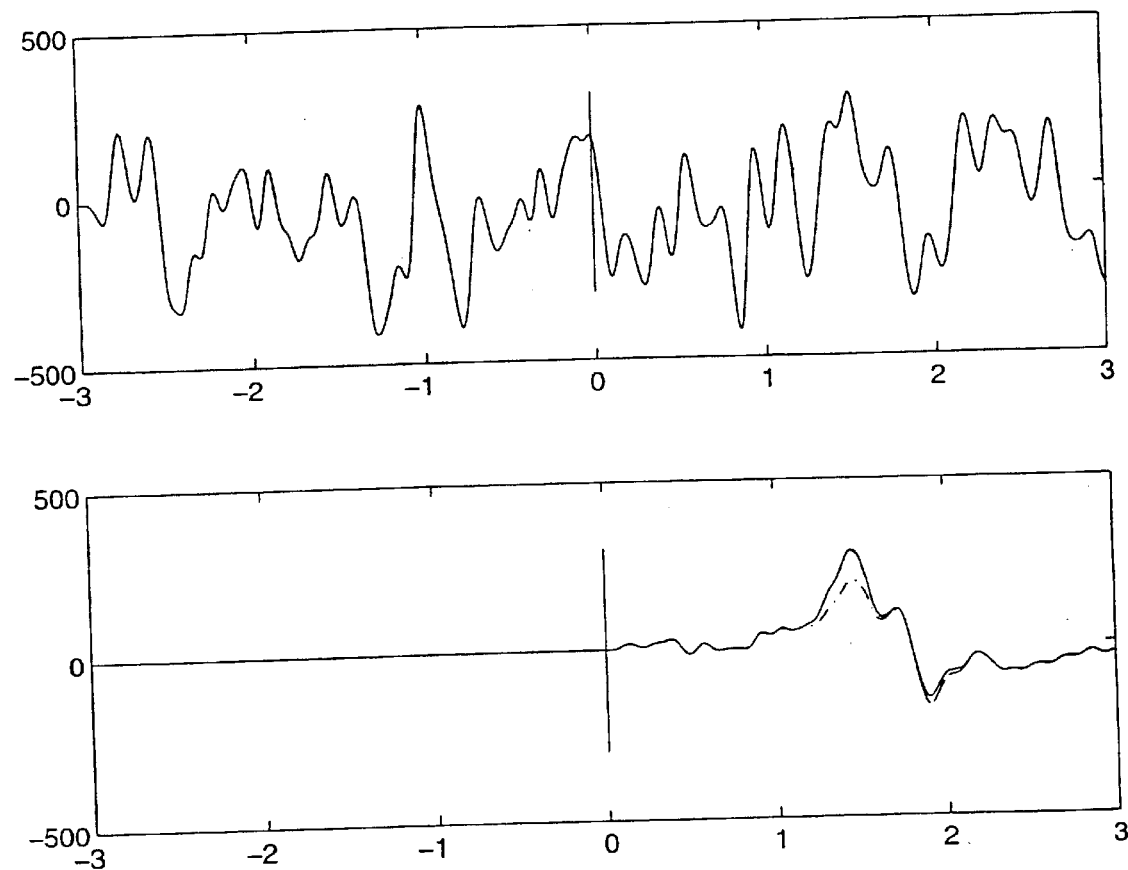

Noting that the decomposition process yields components that are inherently of a lower energy than the total template energy, a higher SNR is required to obtain equivalent performance. For example, if we divide the template into five components with roughly equal energies, the estimation variances for each component would increase by a factor of 5. Noting that an initial SNR of −15 dB yields variances of 5% for the full template, an SNR of −10 dB would be required to obtain 5% variances with five components. Therefore, the next simulation which deals with estimation of five components, is carried out under −10 dB SNR conditions rather than −15 dB. The following simulation demonstrates the estimator's ability to reconstruct a signal which differs from the template both in latency and in amplitude of a single component. FIG. 19 shows a typical movement related potential template and its component-wise decomposition into five components: top—template, bottom—template decomposition. This signal is used for synthesizing the test case explored in the following simulation, where an EP is synthesized from a linear combination of temporally shifted components. FIG. 20 presents the outcome of applying the estimator to a simulated single-trial at a low SNR of −10 dB, where the second peak has been multiplied by 1.5 and advanced by 3 sample points. In the simulation of FIG. 20, the top illustrates a simulated single trial (SNR≈−10 dB), whereas the bottom illustrates the buried and reconstructed signals. In accordance with the results of the previous simulation, a good reconstruction of the morphologically different signal is achieved, which practically coincides with the buried signal. Consistency was also confirmed by comparing the template with the average of 200 signal reconstructions, carried out with a deterministic signal embedded within different noise realizations.

The estimation capabilities of the suggested method were demonstrated, emphasizing the relation between the SNR, decomposition extent (number of components), and variance of estimation. Similar considerations should be made in the analysis of experimental data, ensuring that the appropriate conditions for successful operation of the estimator apply.

6.5 Experimental Results

In the following we shall demonstrate the estimator's performance with two applications. The first deals with motor potentials accompanying free finger movements versus suddenly loaded movements, uncovering a significant component related to the sudden loading. The second application demonstrates the outcome of a well-known odd-ball paradigm, revealing dynamic features of the single-trial evoked potentials correlated with the reaction time of the subject.

Figure 21:
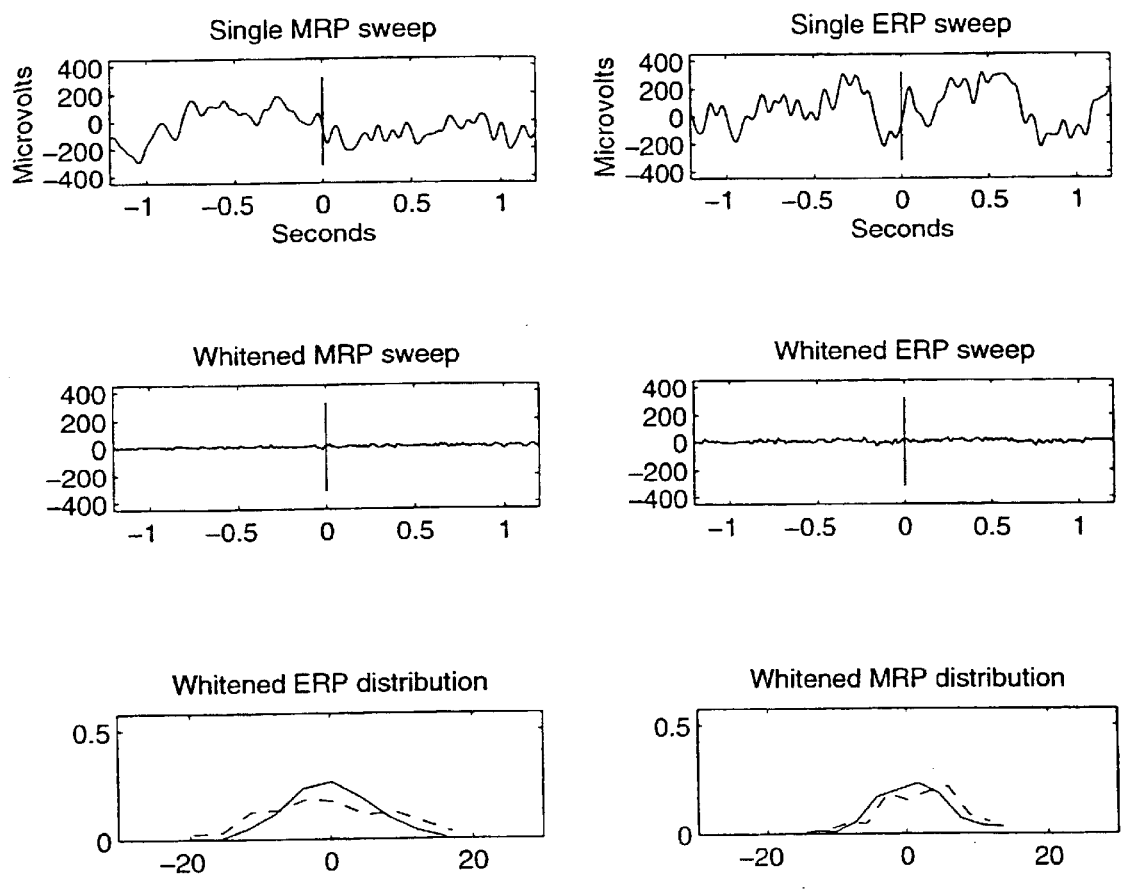

The statistical evaluation has shown that the estimation bias and variance are proportional to the mean and variance of the whitened signal. Stationarity of the mean is guaranteed since the signals are band-passed prior to sampling; therefore it is sufficient to verify that the post-stimulus signal variance is reduced significantly compared to the original signal, its effect on the estimation variance reflected directly from Eq. 52. FIG. 21 presents an example of the whitening results of single MRP and ERP signals, using a pre-stimulus adapted AR filter: top—raw sweeps, middle: whitened sweeps, bottom—whitened signal distributions. It is observed that with both signals, the whitening filter obtained from the pre-stimulus interval is sufficient to whiten the post-stimulus signal; the mean value is practically zero and the variance of the signals reduces by two orders of magnitude due to the whitening, with a similar reduction in the pre- and post-stimulus signals [Madhaven, 1992]. Approximate Gaussianity of the whitened signals is also demonstrated via the whitened ERP and MRP distributions.

6.5.1 Movement Related Potentials

Figure 22:
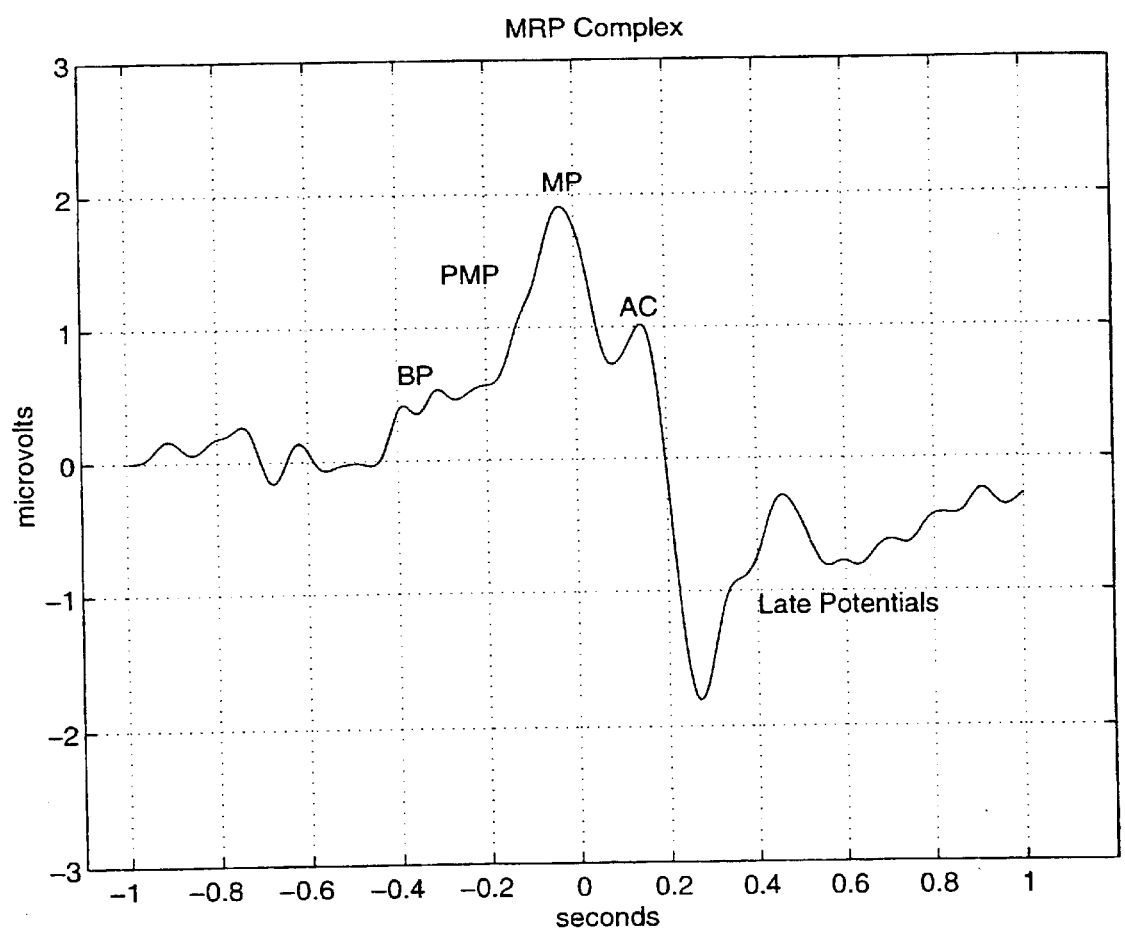

Averaging methods reveal relationships between specific components of MRP's and actual movement parameters. We wish to test whether such effects could be described on a single-trial basis, which would thus improve the existing analysis tools by enabling dynamic tracking of time-varying features. We used evoked potential data recorded during a self-paced finger flexion experiment, recorded differentially between $C_3$ and $C_4$ according to the conventional 10–20 electrode placement system, sampled at 250 Hz and decimated by a factor of 3 prior to processing. The self-paced movements were occasionally disturbed by a mechanical device without prior knowledge of the subject, who was blindfolded during the experiment. The average response is presented in FIG. 22, illustrating this grand average.

Figure 23:
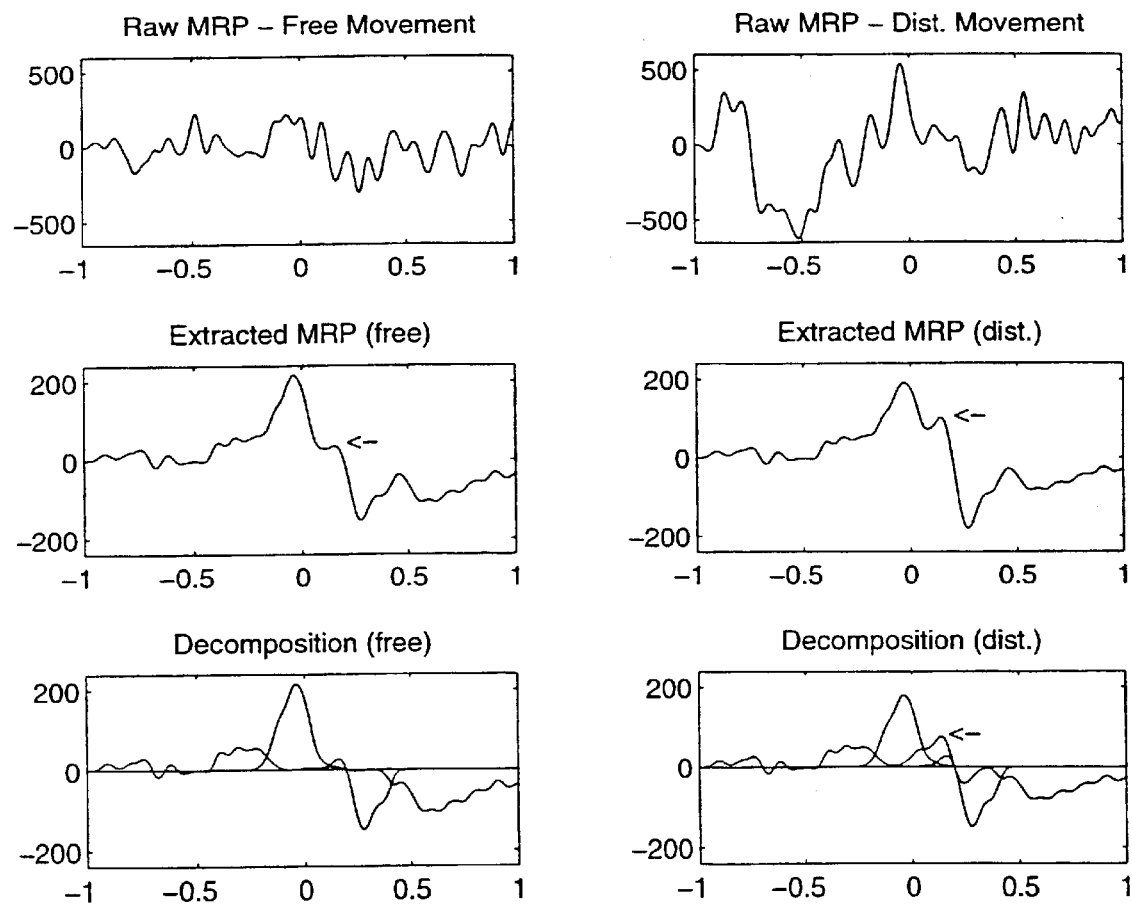

In order to study the effect of the sudden loading, we applied the estimator to two classes of responses—those measured during free (unloaded) movements vs. disturbed (loaded) movements. Comparing the estimation results of the EP's during free and disturbed movements, revealed a unique peak appearing at about 150 msec after movement onset with the disturbed movements only (FIG. 23). This unique peak seems to be in response to the afferent proprioceptive feedback informing the brain of the change of load. This result, which resembles results of similar tests carried out with averaging techniques [Kristeva et. al., 1979], motivated us to further pursue this line of investigation and try to track dynamic signal variations under a well-known experimental paradigm. Since cognitive evoked potentials have been studied extensively for a long time, and recordings are easily accessible, cognitive potentials were chosen for the next test.

6.5.2 Event Related Potentials

Figure 24:
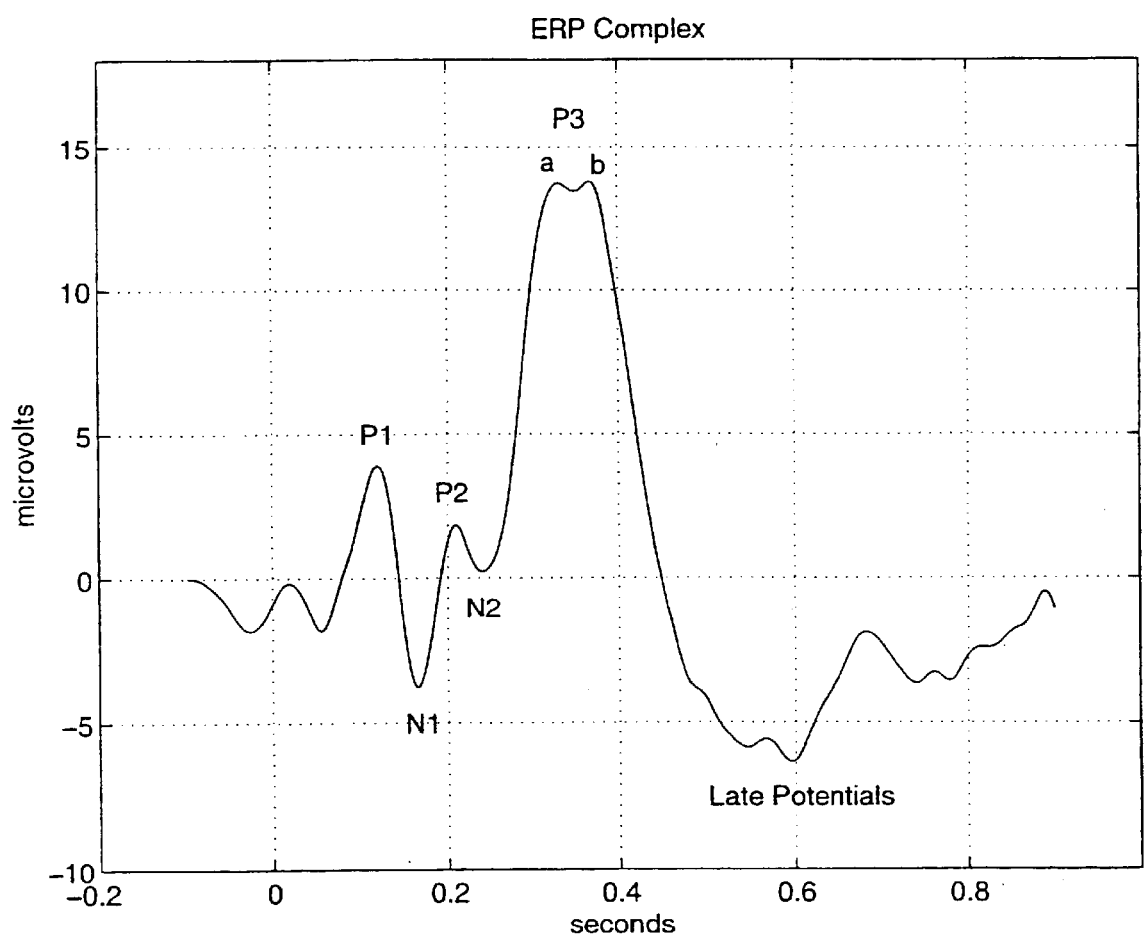
Figure 25:
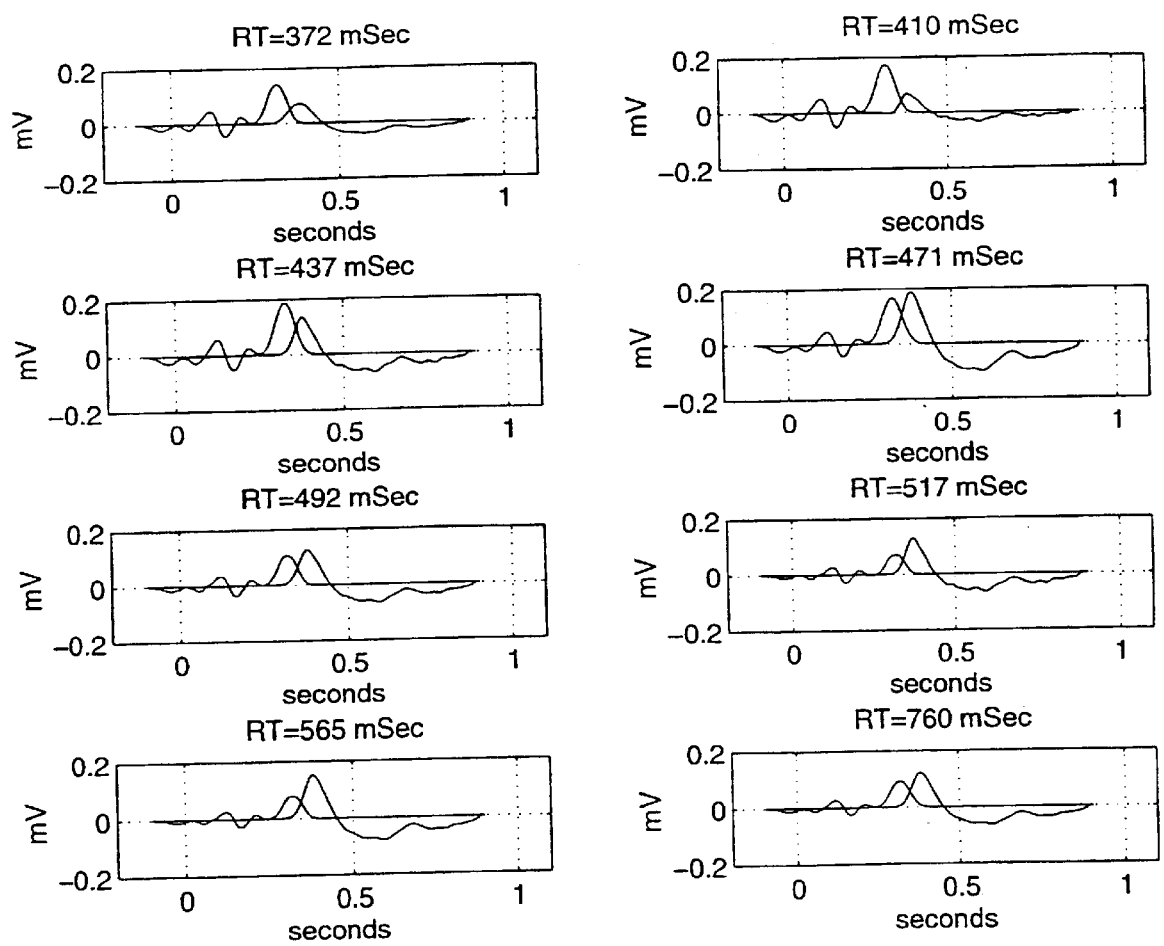

The main motivation for the development of the EP estimation system was to facilitate trial-by-trial tracking of evoked potentials. To demonstrate tracking performance, we apply the estimator to cognitive evoked potential data recorded from $P_z$ referenced to the mid-lower jaw [Jasper, 1958], during a typical odd-ball type paradigm. A detailed description of the experiment can be found in [Lange et. al., 1995]. In addition to the evoked potential data, reaction times to target stimuli were noted in attempt to establish a relation between behavioral performance measures and the $P_{300}$ complex. In a previous analysis which was reported in [Lange et. al., 1995], we found that the latency of the $P_{300}$ component increased with the increase in reaction time. This provides one possible explanation to the appearance of two peaks in the averaged response as demonstrated in FIG. 24. Similar results are commonly reported in ERP literature. However, applying the current estimation procedure, while identifying $P_{300a}$ and $P_{300b}$ to be two distinctive components, yields a different result as can be seen in FIG. 25. In this case, it seems that rather than a change in the latency of $P_{300}$, we obtain a reciprocal change of magnitude of each sub $P_{300}$ component: with the increase in reaction time $P_{300a}$ decreases and $P_{300b}$ increases. This result may be due to the relation between attention allocation and prompt performance; with the drop in attention, reflected by decreased amplitude $P_{300a}$ and resulting in prolonged reaction times, computation, reflected by $P_{300b}$, is delayed but increased in amplitude. This effect may indicate compensation for decreased attention by increased computational effort. This result is also in accordance with limited findings in ERP literature, which differentiate the positive $P_{300}$ component into two constituents, based on averaged EP's recorded during cognitive experimentation [Verleger & Wascher, 1995]. Interestingly, the estimator has identified changes of respective component amplitudes without change of latencies, even though it can compensate for latency variations of single components.

We have thus shown that dynamic variations of evoked potential components which may not be detectable from the averaged data, can be extracted from the raw data using the suggested estimation method, overcoming the severe problems of a low SNR and temporally overlapping signal components.

6.6 Discussion

A parametric model for extraction of single evoked potential components was presented. The model utilizes the information extracted in the previous processing layers, extracting the single-trial EP from the recorded noisy measurement using the pre-stimulus ongoing EEG activity as a model of the post-stimulus activity, and a decomposed EP library item as a model of the constituent components in the single EP waveform.

The estimator was analyzed analytically and via simulation, verifying its ability to extract transient responses with overlapping spectra down to SNR's of around −20 dB. Numerical problems were not encountered using the explicit formulas, yet alternative numerical techniques available for computing least-square estimates may be employed if necessary [Golub & Van Loan, 1983].

The dependence of the estimation accuracy on the extent of decomposition was demonstrated, describing the increase in estimation variance as the ratio between the signal and noise energy decreases; the tradeoff between template energy and estimation variance was presented analytically, elucidating the effect of over-decomposition on the reliability of estimation. This tradeoff should be considered in the design of experimental paradigms and variability analysis requirements.

The estimator's performance with real data has demonstrated its ability to identify morphological variations of single evoked potential responses, e.g. displaying a unique difference between MRP's due to application of an external mechanical disturbance, and a gradual reciprocal change of ERP components corresponding to the subject's performance.

7 Discussion and Conclusion

7.1 Summary

In this work I described the development of a novel processing system of evoked brain potentials, which resulted in a comprehensive framework for the analysis of trial-varying brain responses. The main contribution of the proposed framework lies in its ability to extract potentially variable single-trial brain responses, which has been the major focus of this work.

Contrary to common single-trial methods, which start off with the average EP serving as a reference signal, the proposed method initiates the processing with autonomous identification of the embedded response types. These types constitute a library of evoked responses, encapsulating the major variability of the embedded responses. Then, a statistical approach is used to decompose each of the library items into a set of distinctive components, whose attributes (latency and amplitude) are adaptively manipulated to model deviations of the single responses from their respective parent library items. Finally the single responses are emulated from the decomposed library items to best fit the recorded sweeps.

The processing framework was evaluated layer by layer via computer simulations, yielding successful results in extracting the simulated single-trial responses. The system was then used to extract variable brain responses from several experimental sessions, resulting in physiologically justifiable and consistent findings. These results encourage further examination of the processing framework, with additional types of brain responses, which might contribute towards the development of modern single-trial analysis standards to replace the old-fashioned averaging based methods.

7.2 Discussion

The processing begins with spontaneous identification of the EP response types, embedded within the ensembled data. The identification process can be implemented on line in real time, with a continuous dynamic update of the the response types. The current implementation is based on a fixed network structure, requiring a-priori selection of the network size which corresponds to the anticipated size of the response library. Preliminary studies have shown that the network can adapt its own structure by increasing or decreasing its dimension; a possible criterion for such dynamic behavior is the degree of correlation among the various library items, that is, the network may increase until no significant changes of the obtained items can be observed.

The single evoked responses are modeled as a sum of several components, derived from the library of parent responses. Responses associated with the same parent waveform may differ one from another due to amplitude and latency variations of the constituent components. The set of components is related to both sequential and parallel neuronal processing stages, distinguished by manipulating the experimental paradigm to produce independent variations of the different components. The separation of the signal into distinct components is based on a statistical approach, assuming Gaussian distributed neural activity, yielding a set of components which sum up exactly to the original waveform. The separation process is robust to major violations of the assumptions, e.g. non-Gaussian or non-symmetrical components. It should be noted that different assumptions regarding neural activity, if found more appropriate, may easily be incorporated in the model by substitution of the statistical neural activation hypothesis with an alternative hypothesis.

The single-trial EP is obtained using a parametric model, utilizing the information extracted via the previous processing layers. Despite the poor SNR, the model is able to predict the measured process, resulting in the identification of its two assumed contributions: the ongoing EEG and the embedded EP. Significant non-stationarities of the background EEG are not likely to appear during the relatively short analysis time-frame. Although phase-locking effects are not uncommon (e.g. alpha-locking with sensory stimulation), such effects tend to decay within 2–3 tenths of a second after stimulus presentation and should not have a significant effect on the estimation performance. With our data, both ERP's and MRP's were not accompanied by major statistical EEG variability; nevertheless, robust estimation of post-stimulus background EEG may be employed to overcome severe non-stationarities if such are encountered [Birch et. al., 1993].

Component smearing due to latency variations was not considered, however it may be considerably corrected for by component realignment throughout the ensemble using the identified lag of each component, after which an improved template may be obtained by processing the realigned data, similar to common realignment procedures [e.g. Spreckelsen & Bromm, 1988]. In addition, artifacts due to eye movements may be eliminated by adding an appropriate input channel whose contribution should be adaptively subtracted from the estimated response, as described in [Cerutti et. al., 1987].

The system was applied to two major types of EP's: Movement Related Potentials (MRP's) and cognitive Event Related Potentials (ERP's). In both cases the system was able to extract the single-trial brain responses, the analysis of which revealed dynamic behavior of the responses, like the afferent peak appearing with loaded movements in MRP's, and a reciprocal change of cognitive components correlated with performance indices (reaction time) in ERP's. Moreover, it has been shown that selective averaging may not be adequate, as demonstrated in the case of ERP's, where some of the Non-Target responses presented similar characteristics to the Target responses. Such effects could not be detected with averaging techniques, nor with single-trial methods relying on the average response as a reference signal. The ability to objectively track EP variations on a single-trial basis, as presented in the experimental results throughout this work, emphasizes the added value of using the framework described herein.

7.3 Conclusion

Current single-trial EP processing methods are usually restricted to average-like single-trial estimates, or use EEG non-stationarities as indices to EP manifestations. While the first approach is not flexible in the sense that single-trial EP's which do not resemble to the template will not be detected, the second approach is over-sensitive as it might associate 'non-conforming' EEG's with 'contaminating' EP's.

The processing framework proposed herein is to some extent a compromise between the two above approaches, as it is not limited to average-like responses on the one hand yet it is not sensitive to EEG non-stationarities on the other hand. The multi-layer processing approach provides a flexible yet robust estimation performance, enabling extraction of the low SNR, trial varying evoked brain responses and tracking of their constituent components. The association of such components with their neuroelectric origins may significantly contribute to the understanding of the genesis of the observed signals and thus lead to elucidation of the complicated processes occurring in the central nervous system.

While the invention has been described above with respect to a particular application?, it will be appreciated that these are set forth merely for purposes example, and that many other variations, modofications and applications of the invention may be made.

List of Symbols

EP—Evoked Potential
ERP—Event Related Potential
EEG—ElectroEncephaloGram
SNR—Signal to Noise Ratio
MSE—Mean Square Error
AR—Auto Regressive
ARX—Auto Regressive with Exogenous Input
ANN—Artificial Neural Network
$E[\cdot]$—Expectancy
I—Identity matrix
N—Number of processed single-trials
P—Number of competing neurons
i—Trial index
x,y—Single-trial recordings
E—Signal energy
s—Normalized EP waveform
e—Backgroung EEG
o—Neural output
w—Neural weight vector
$\eta$—Learning rate coefficient
$\rho$—Weight rate-of-change coefficient
$\sigma$—Noise RMS
$\alpha$—Distortion coefficient
$\tau$—Learning cycle time constant
$\Gamma$—Classification confidence coefficient
C—Covariance Matrix
$T_j$—Template of the j-th component
$v_j$—Normalized j-th component waveform
$k_j$—Amplitude gain factor of the j-th component
$A_t$—Set of firing neurons at time instant t
$A_t^j$—Set of firing neurons contributing to the j-th component
$d_j$—Firing instant distribution of the j-th component neural source
$A(z), B(z)$—FIR filters
$\epsilon$—Whitened EEG References

[1] M. Abeles, Y. Prut, E. Vaadia, and A. Aertsen, "Integration, synchronicity and periodicity," in *Brain Theory: Spatio-Temporal Aspects of Brain Function*, A. Aertsen Ed., Elsevier Science Publishers B.V., 1993, pp. 149–181.

[2] H. Akaike, "Statistical predictor identification," *Ann. Inst. Stat. Math.*, vol. 22, pp. 203–217. 1970.

[3] J. I. Aunon, C. D. McGillem, and D. G. Childers, "Signal processing in evoked potential research: averaging and modeling," *CRC Crit. Rev. Bioeng.*, vol. 5, pp. 323–367, 1981.

[4] E. A. Bartnik, K. J. Blinowska, and P. J. Durka, "Single evoked potential reconstruction by means of wavelet transform," *Biol. Cybern.*, vol 67, pp. 175–181, 1992.

[5] H. A. Beagly, B. M. Sayers, and A. J. Ross, "Fully objective ERA by phase spectral analysis," *Acta Otolaryngol*, vol. 87, pp. 270–278, 1979.

[6] G. E. Birch, P. D. Lawrence, and R. D. Hare, "Single-trial processing of event related potentials using outlier information," *IEEE Trans. Biomed. Eng.*, vol. 40, pp. 59–73, 1993.

[7] G. E. P. Box and G. M. Jenkins, *Time series analysis: forecasting and control*. San Francisco, Calif.: Holden-Day, 1976.

[8] E. H. Carlton and S. Katz, "Is wiener filtering an effective method of improving evoked potential estimation?," *IEEE Trans. Biomed. Eng.*, vol. 34, No 1, 1987.

[9] S. Cerutti, G. Baselli, D. Liberati, G. Pavesi, "Single sweep analysis of visual evoked potentials through a model of parametric identification," *Biol. Cybernetics*, vol. 56, pp. 111–120, 1987.

[10] S. Cerutti, G. Chiarenza, D. Liberati, P. Mascellani, and G. Pavesi, "A parametric method of identification of single trial event related potentials in the brain," *IEEE Trans. Biomed. Eng.*, vol. 35, pp. 701–711, 1988.

[11] K. H. Chiappa, *Evoked potentials in clinical medicine*. New York: Raven, 1983.

[12] V. H. Clarson and J. J. Liang, "Mathematical classification of evoked potential waveforms," *IEEE Trans. Sys. Man & Cybern.*, vol. 19, pp. 68–73, 1989.

[13] A. M. Dale and M. I. Sereno, "Improving localization of cortical activity by combining EEG and MEG with MRI cortical surface reconstruction: a linear approach," *Journal of Cognitive Neuroscience*, vol. 5, 162–176, 1993.

[14] J. P. C. de Weerd, "A posteriori time-varying filtering of averaged evoked potentials. I. Introduction and conceptual basis," *Biol. Cybern.*, vol. 41, pp. 211–222, 1981.

[15] L. Deecke, B. Grozinger, and H. H. Kornhuber, "Voluntary finger movement in man: cerebral potentials and theory," *Biol. Cybernetics*, vol. 23, pp. 99–119, 1976.

[16] E. Donchin, "A Multivariate approach to the analysis of average evoked potentials," *IEEE. Trans. Biomed. Eng.*, vol. 13, 1966.

[17] E. Donchin and E. Heffley, "Multivariate analysis of event-related potential data: a tutorial review," in *Multidisciplinary perspectives in event-related brain potential research*, D. Otto (Ed.), Washington D.C.: Government Printing Office, 1978.

[18] D. J. Doyle, "Some comments on the use of wiener filtering in the estimation of evoked potentials," *Electroencephalogr. Clin. Neurophysiol.*, vol. 28, pp. 533–534, 1975.

[19] R. O. Duda and P. E. Hart. *Pattern classification and scene analysis*. Wiley: New-York, 1976.

[20] L. A. Farwell and E. Donchin, "Taking off the top of your head: toward a mental prosthesis utilyzing event-related potentials," *Electroencephalogr. Clin. Neurophysiol.*, vol. 70, pp. 510–523, 1988.

[21] L. A. Farwell and E. Donchin, "The truth will out: Interrogative polygraphy with event related brain potentials," *Psychophysiology*, vol. 28, 1991.

[22] J. A. Freeman and D. M. Skapura. *Neural networks: Algorithms, applications, and programming techniques*: Addison-Wesley Publishing Company, USA, 1992.

[23] M. Furst and A. Blau, "Optimal a-posteriori time domain filter for average evoked potentials," *IEEE Trans. Biomed. Eng.*, vol. 38, pp. 827–833, 1991.

[24] W. Gersch, "Spectral analysis of EEG's by autoregressive decomposition of time series," *Math. Biosc.* vol. 7, pp. 205–222, 1970.

[25] A. S. Gevins, "Analysis of the electromagnetic signals of the human brain: milestones, obstacles and goals," *IEEE Trans. Biomed. Eng.*, vol. 31, pp. 833–850, 1984.

[26] A. S. Gevins, N. H. Morgan, S. L. Bressler, J. C. Doyle, and B. A. Cutillo, "Improved event related potential estimation using statistical pattern classification," *Electroencephalogr. Clin. Neurophysiol.*, vol. 64, pp. 177–186, 1986.

[27] G. H. Golub and C. F. Van Loan, *Matrix computations*. Johns Hopkins University Press, Baltimore, Md., 1983.

[28] L. Gupta, D. L. Molfese, R. Tammana, and P. G. Simos, "Nonlinear alignment and averaging for estimating the evoked potential," *IEEE Trans. Biomed. Eng.*, vol. 43, pp. 348–356, 1996.

[29] S. Haykin, *Adaptive filter theory*. Prentice-Hall: N.J., 1986.

[30] S. Haykin. *Neural Networks: A Comprehensive Foundation*: Macmillan College Publishing Company, Inc., USA, 1994.

[31] J. Hertz, A. Krogh, and R. G. Palmer. *Introduction to the theory of neural computation*. Addison-Wesley Publishing Company, USA, 1991.

[32] H. H. Jasper, "The ten-twenty electrode system of the international federation," *Electroenc. Clin. Neurophysiol*, vol. 10, pp. 371–375, 1958.

[33] J. P. Kaipio and P. A. Karjalainen, "Estimation of event related synchronization changes by a new tvar method," *IEEE Trans. Biomed. Eng.*, vol. 44, pp. 649–656, 1997.

[34] X. Kong and N. V. Thakor, "Adaptive Estimation of Latency Changes in Evoked Potentials," *IEEE Trans. Biomed. Eng.*, vol. 43, pp. 189–197, 1996.

[35] R. Kristeva, D. Cheyne, W. Lang, G. Lindinger, and L. Deecke, "Movement related potentials accompanying unilateral and bilateral finger movements with different inertial loads," *Electroencephalogr. Clin. Neurophysiol*, vol. 75, pp. 410–418, 1979a.

[36] R. Kristeva, E. Keller, L. Deecke and H. H. Kornhuber, "Cerebral potentials preceding unilateral and bilateral simultaneous finger movement," *Electroencephalogr. Clin. Neurophysiol.*, vol. 47, pp. 229–238, 1979b.

[37] P. Laguna, R. Jane', O. Meste, P. W. Poon, P. Caminal, H. Rix, and N. V. Thakor, "Adaptive filter for event-related bioelectric signals using an impulse correlated reference input: comparison with signal averaging techniques," *IEEE Trans. Biomed. Eng.*, vol. 39, pp. 1032–1043, 1992.

[38] D. H. Lange, H. Pratt, and G. F. Inbar, "Segmented matched filtering of singe event related evoked potentials," *IEEE Trans. Biomed. Eng.*, vol. 42, pp. 317–321, 1995.

[39] D. H. Lange and G. F. Inbar, "A robust parametric estimator for single-trial movement related brain potentials," *IEEE Trans. Biomed. Eng.*, vol. 43, pp. 341–347, 1996a.

[40] D. H. Lange and G. F. Inbar. "Parametric modeling and estimation of amplitude and time shifts in single evoked potential components". In *Advances in Processing and Pattern Analysis of Biological Signals*, I. Gath and G. F. Inbar, Eds. Plenum Press: 1996b.

[41] D. H. Lange and G. F. Inbar, "Brain-wave based polygraphy," in *Proc. IEEE EMBS96*, Amsterdam, 1996c.

[42] D. H. Lange, H. Pratt, and G. F. Inbar, "Modeling and estimation of single evoked brain potential components," *IEEE Trans. Biomed. Eng.*, vol. 44, pp. 791–799, 1997.

[43] D. H. Lange, H. T. Siegelman, H. Pratt, and G. F. Inbar, "A generic approach for identification of event related brain potentials via a competitive neural network structure," to appear in *Proc. NIPS*97—Neural Information and Processing Systems: Natural & Synthetic*, 1998.

[44] D. Liberati, S. DiCorrado, and S. Mandelli, "Topographic mapping of single sweep evoked potentials in the brain," *IEEE Trans. Biomed. Eng.*, vol. 39, pp. 943–951, 1992.

[45] P. G. Madhaven, "Minimal repetition evoked potential by modified adaptive line enhancement," *IEEE Trans. Biomed. Eng.*, vol. 39, pp. 760–764, 1992.

[46] J. Makhoul, "Linear prediction: a tutorial review," *Proc. IEEE*, vol. 63, 1975.

[47] S. G. Mason, G. E. Birch, and M. R. Ito, "Improved single-trial signal extraction of low SNR events," *IEEE Trans. Sig. Proc.*, vol. 42, pp. 423–426, 1994.

[48] G. McCarthy and E. Donchin, "A Metric for Thought: A Comparison of $P_{300}$ Latency and Reaction Time," *Science*, vol. 211, pp. 77–80, 1981.

[49] H. J. Michalewski, D. K. Prasher, and A. Starr, "Latency variability and temporal interrelationships of the auditory event-related potentials (N1,P2,N2, and P3) in normal subjects," *Electroenc. Clin. Neurophysiol.*, vol. 65, pp. 59–71, 1986.

[50] O. Meste and H. Rix, "Jitter statistics estimation in alignement processes," *Signal Processing*, vol. 51, pp. 41–53, 1996.

[51] J. M. Moser and J. I. Aunon, "Classification and detection of single evoked brain potentials using time-frequency amplitude features," *IEEE Trans. Biomed. Eng*, vol. 33, pp. 118–127, 1986.

[52] M. Nakamura, "Waveform estimation from noisy signals with variable signal delay using bispectrum averaging," *IEEE Trans. Biomed. Eng.*, vol. 40, pp. 118–127, 1993.

[53] P. L. Nunez, *Electric fields of the brain*. Oxford University Press, 1981.

[54] T. W. Picton and S. A. Hillyard, "Endogenous event related potentials," in *Handbook of electroencephalographic clinical neurophysiology*," vol. 3, T. W. Picton, Ed. Amsterdam: Elsevier, 1988, pp. 361–426.

[55] D. Popivanov and I. Krekule, "Estimation of homogenity of a set of evoked potentials with respect to its dispersion," *Electroencephalogr. Clin. Neurophysiol.*, vol. 55, pp. 606–608, 1983.

[56] H. Pratt, H. J. Michalewski, G. Barrett, and A. Starr, "Brain potentials in memory-scanning task: modality and task effects on potentials to the probes," *Electroencephalogr. Clin. Neurophysiol.*, vol. 72, pp. 407–421, 1989.

[57] M. A. Rodriguez, R. H. Williams, and T. J. Carlow, "Signal delay and waveform estimation using unwarpped phase averaging," *IEEE Trans. Acoust. Sp. & Sig. Proc.*, vol. 29, pp. 508–513, 1981.

[58] O. Rompelman and H. H. Ros, "Coherent averaging technique: a tutorial review. Part 1: Noise reduction and the equivalent filter," *J. Biomed. Eng.*, vol. 8, pp. 24–29, 1986a.

[59] O. Rompelman and H. H. Ros, "Coherent averaging technique: a tutorial review. Part 2: Trigger jitter, overlapping responses and non-periodic stimulation" *J. Biomed. Eng.*, vol. 8, pp. 30–35, 1986b.

[60] A. V. Roterdam, "Limitations and difficulties in signal processing by means of the principal component analysis," *IEEE Trans. Biomed. Eng.*, vol. 17, pp. 268–269, 1970.

[61] D. E. Rumelhart and D. Zipser, "Feature discovery by competitive learning," *Cognitive Science*, vol. 9, pp. 75–112, 1985.

[62] V. L. Schwent and S. A. Hillyard, "Evoked potential correlates of selective attention with multi-channel auditory inputs," *Electroencephalogr. Clin. Neurophysiol.*, vol. 38, pp. 131–138, 1975.

[63] M. V. Spreckelsen and B. Bromm, "Estimation of single-evoked cerebral potentials by means of parametric modeling and kalman filtering," *IEEE Trans. Biomed. Eng.*, vol. 35, pp. 691–700, 1988.

[64] O. Svensson, "Tracking of changes in latency and amplitude of the evoked potential by using adaptive LMS filters and exponential averagers," *IEEE Trans. Biomed. Eng.*, vol. 40, pp. 1074–1079, 1993.

[65] N. V. Thakor, "Adaptive filtering of evoked potentials," *IEEE Trans. Biomed. Eng.*, vol. 34, pp. 6–12, 1987.

[66] N. V. Thakor, X. R. Guo, C. A. Vaz, P. Laguna, R. Jane, P. Caminal, H. Rix, and D. F. Hanley, "Orthonormal (Fourier and Walsh) models of time varying evoked potentials in neurological injury," *IEEE Trans. Biomed. Eng.*, vol. 40, pp. 213–221, 1993.

[67] H. G. Vanghan, Jr. and J. C. Arezzo, "The neural basis of event related potentials," in Handbook of *Electroenceph. and Clin. Neurophysiol.*, vol 3, T. W. Picton Ed., Amsterdam: Elsevier 1988, pp. 45–87.

[68] R. S. Varga, *A decomposition technique for signals overlapping in time*. Ph. D. dissertation, University of Florida, 1969.

[69] C. A. Vaz and N. V. Thakor, "Adaptive fourier estimation of time-Varying evoked potentials," *IEEE Trans. Biomed. Eng.*, vol. 4, pp. 448–455, 1989.

[70] R. Verleger and E. Wascher, "Fitting ex-Gauss functions to P3 waveshapes: an attempt at distinguishing between real and apparent changes of P3 latency," *Journal of Psychophysiology*, vol. 9, pp. 146–158, 1995.

[71] D. O. Walter, "A posteriori wiener filtering of average evoked responses," *Electroencephalogr. Clin. Neurophysiol.*, suppl., vol. 27, pp. 61–70, 1969.

[72] C. D. Woody, "Characterization of an adaptive filter for the analysis of variable latency neuroelectric signals," *Med. & Biol. Eng.*, vol. 5, pp. 539–553, 1967.

[73] K. Yu and C. D. McGillem, "Optimum filters for estimating evoked potential waveforms," *IEEE Trans. Biomed. Eng.*, vol. 30, pp. 730–737, 1983.

What is claimed is:

1. A method of extracting low SNR signals from noise comprising the following steps:
   a) dynamically identifying, via a competitive neural network, various transient response types embedded within a recorded ensemble of composite signals;
   b) decomposing the response types;
   c) constructing a parametric synthesis model that emulates a single-sweep signal generation mechanism.

2. The method of claim 1 further comprising the step of:
   taking a single sweep composite signal, identifying its response type, filtering its corresponding decomposed components through the parametric synthesis model's filters and summing the resulting filtered components to extract an evoked potential.

3. The method of claim 2 wherein said method extracts an evoked potential appearing in an electroencephalogram.

4. The method of claim 2 wherein said method further comprises the step of displaying said evoked potential.

5. The method according to claim 1, wherein said process (a) is performed by using an adaptive, competitive neural network.

6. The method according to claim 2, wherein said neural network includes a group of artificial neurons divided into sets of inhibitory clusters in which all neurons within a cluster inhibit all other neurons in the cluster, resulting in a competition among the neurons in a cluster to respond to the major transient signal patterns in the composite signal.

7. The method according to claim 2, wherein said process (a) includes:
   (i) initializing network weights;
   (ii) selecting one input vector at random;
   (iii) calculating all neural outputs in selecting a winner neuron;
   (iv) updating the winning neuron weights;
   (v) repeating the foregoing steps until a stopping criterion is achieved; and
   (vi) displaying the identified signal types.

8. The method according to claim 1, wherein said decomposing process (b) is performed by treating peaks of the composite signal as independent components and analyzing said peaks.

9. The method according to claim 5, wherein said process (b) includes:
   (i) initializing search limits;
   (ii) calculating peak locations;
   (iii) optimizing first and second peak moments;
   (iv) building a decomposition rule;
   (v) executing a decomposition procedure to identify signal types; and
   (vi) displaying the identified signal types.

10. The method according to claim 1, wherein said synthesizing process (c) is performed by modeling the EEG via auto regressive (AR) analysis and modeling EP as a sum of finite impulse responses (FIR) filtered EP components.

11. The method according to claim 7, wherein said synthesizing process (c) includes:
   (i) assigning transition points;
   (ii) building an AR model of the pre-stimulus EEG signal;
   (iii) whitening the EEG and EP signals;
   (iv) identifying the EP by performing a closed form least square solution of the model; and
   (v) extracting the EP signal.

12. An apparatus for extracting low SNR signals from noise comprising:
   a competitive neural network transient response identifier;
   a response type decomposition unit;
   a parametric synthesis model that emulates a single-sweep signal generation mechanism.

13. The apparatus of claim 12 further comprising:
   an evoked potential extractor including a single sweep composite signal procurer;
   a response type identifier;
   parametric synthesis model decomposed component filters; and
   a filtered components summer.

14. The apparatus according to claim 13, wherein said neural network includes a group of artificial neurons divided into sets of inhibitory clusters in which all neurons within a cluster inhibit all other neurons in the cluster, resulting in a competition among the neurons in a cluster to respond to the major transient signal patterns in the composite signal.

15. The apparatus according to claim 13, wherein said identifier:
   (i) initializes network weights;
   (ii) selects one input vector at random;
   (iii) calculates all neural outputs in selecting a winner neuron;
   (iv) updates the winning neuron weights; and
   (v) repeats the foregoing steps until a stopping criterion is achieved.

16. The apparatus according to claim 12, wherein said decomposition unit operates by treating peaks of the composite signal as independent components and analyzing said peaks.

17. The apparatus according to claim 12, wherein said decomposition unit:
   (i) initializes search limits;
   (ii) calculates peak locations;
   (iii) optimizes first and second peak moments;
   (iv) builds a decomposition rule; and
   (v) executes a decomposition procedure to identify signal types.

18. The apparatus according to claim 12, wherein the low SNR transient signal is a transient evoked potential (EP) appearing in an electroencephalogram (EEG) of a living being generated in response to sensory stimulation of the nervous system of the living being.

19. The apparatus according to claim 18, wherein said a parametric synthesis model models the BEG via an AR analysis, and models the EP as a sum of the FIR filtered EP components.

20. The apparatus according to claim 17, wherein said parametric synthesis model:
   (i) assigns transition points;
   (ii) builds an AR model of the pre-stimulus BEG signal;
   (iii) whitens the EEG and EP signals;
   (iv) identifies the EP by performing a closed form least square solution of the model; and
   (v) extracts the EP signal.

21. The apparatus according to claim 12, wherein said identifier, said decomposition unit, and said model are in the form of computer software.

22. A method for extracting an evoked potential comprising the steps of:
   obtaining a single sweep composite signal using an adaptive, competitive neural network;
   identifying said signal's response type;
   filtering its corresponding decomposed components through the parametric synthesis model filters based upon the model described in claim 1;
   summing the resulting filtered components to extract a transient evoked potential.

23. The method of claim 22 wherein said evoked potential is an evoked potential appearing in an electroencephalogram.

24. An apparatus for extracting an evoked potential comprising:
   a competitive neural network;
   a transient signal response type identifier;
   parametric synthesis model filters based on the model described in claim 1;
   a summer.

25. The apparatus of claim 24 wherein said model of claim 1 models an electroencephalogram signal.

* * * * *